US011459565B2

(12) United States Patent
Martin et al.

(10) Patent No.: US 11,459,565 B2
(45) **Date of Patent: *Oct. 4, 2022**

(54) HIPPO AND DYSTROPHIN COMPLEX SIGNALING IN CARDIOMYOCYTE RENEWAL

(71) Applicants: Baylor College of Medicine, Houston, TX (US); Texas Heart Institute, Houston, TX (US)

(72) Inventors: James F. Martin, Pearland, TX (US); Yuka Morikawa, Houston, TX (US); Todd Ryan Heallen, Houston, TX (US); John Leach, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 26 days.

This patent is subject to a terminal disclaimer.

(21) Appl. No.: 17/096,260

(22) Filed: Nov. 12, 2020

(65) Prior Publication Data

US 2021/0062190 A1 Mar. 4, 2021

Related U.S. Application Data

(63) Continuation of application No. 16/544,209, filed on Aug. 19, 2019, now abandoned, which is a (Continued)

(51) Int. Cl.

*C12N 15/113* (2010.01)
*A61K 31/713* (2006.01)

(Continued)

(52) U.S. Cl.

CPC .......... *C12N 15/113* (2013.01); *A61K 31/713* (2013.01); *C12N 7/00* (2013.01);

(Continued)

(58) Field of Classification Search

CPC .............. C12N 15/113; C12N 15/1137; C12N 2320/30; A61K 31/713

See application file for complete search history.

(56) References Cited

U.S. PATENT DOCUMENTS 6,076,532 A 6/2000 Thomas et al.
6,569,662 B1 5/2003 Tang et al.

(Continued)

FOREIGN PATENT DOCUMENTS

WO 2010039778 A2 4/2010

OTHER PUBLICATIONS

Fei Xu et al. "Mammalian sterile 20-like kinase 1/2 inhibits the Wntjbeta-catenin signalling pathway by directly binding casein kinase lepsilon", Biochemical Journal, vol. 458, No. 1, Nov. 4, 2013, pp. 159-169.

(Continued)

*Primary Examiner* — Terra C Gibbs
(74) *Attorney, Agent, or Firm* — Norton Rose Fulbright US LLP

(57) ABSTRACT

Embodiments of the disclosure include methods and compositions for the renewal of cardiomyocytes by targeting the Hippo pathway. In particular embodiments, an individual with a need for cardiomyocyte renewal is provided an effective amount of a shRNA molecule that targets the Sav1 gene. Particular shRNA sequences are disclosed.

19 Claims, 8 Drawing Sheets

Specification includes a Sequence Listing.

Related U.S. Application Data continuation of application No. 16/164,550, filed on Oct. 18, 2018, now abandoned, which is a continuation of application No. 15/642,200, filed on Jul. 5, 2017, now Pat. No. 10,119,141, which is a continuation of application No. 15/102,593, filed as application No. PCT/US2014/069349 on Dec. 9, 2014, now Pat. No. 9,732,345.

(60) Provisional application No. 61/913,715, filed on Dec. 9, 2013.

(51) Int. Cl.
*C12N 15/86* (2006.01)
*C12N 7/00* (2006.01)

(52) U.S. Cl.
CPC .......... *C12N 15/86* (2013.01); *C12N 2310/14* (2013.01); *C12N 2310/531* (2013.01); *C12N 2320/30* (2013.01); *C12N 2740/15043* (2013.01); *C12N 2750/14143* (2013.01)

(56) References Cited

U.S. PATENT DOCUMENTS

| | | | |
|---|---|---|---|
| 9,732,345 | B2 | 8/2017 | Martin et al. |
| 10,119,141 | B2 | 11/2018 | Martin et al. |
| 2003/0073623 | A1 | 4/2003 | Drmanac et al. |
| 2003/0194704 | A1 | 10/2003 | Penn et al. |
| 2009/0312251 | A1* | 12/2009 | Lim .................... A61P 35/00 514/8.1 |
| 2012/0252882 | A1 | 10/2012 | Chuah et al. |

OTHER PUBLICATIONS

Fei Xu et al., “Supplementary online data: Mammalian sterile 20-like kinase 1/2 inhibits the Wnt/beta-catenin signalling pathway by directly binding casein kinase lepsilon”, Biochemical Journal, vol. 458, No. 1, Nov. 4, 2013, pp. 159-169.

Heallen et al. “Hippo signaling impedes adult heart regeneration,” Development, Dec. 1, 2013 (Dec. 1, 2013), vol. 140, No. 23, pp. 4683-4690. entire document.

International Search Report and Written Opinion for PCT/US2014/069349 dated Apr. 7, 2015.

Keiko Matsuura et al., “Downregulation of SAV1 plays a role in pathogenesis of high-grade clear cell renal cell carcinoma”, BMC Cancer, Biomed Central, London. GB, vol. 11, No. 1, Dec. 20, 2011, p. 523.

McCulloch A. et al., “000327BMPA003765HT BMPA Bos taurus eDNA 5', mRNA sequence”, Database Embase [Online], Jul. 22, 2008, XP002770621, Database accession No. DY080213, Elsevier Science Publishers. Amsterdam, NL.

SEQ ID No. 175, U.S. Pat. No. 6,569,662 B1 (Tang et al) May 28, 2003 (May 27, 2003). Retrieved from the Internet: on Mar. 9, 2015 (Mar. 9, 2015). entire document.

SEQ ID No. 20999, US 2003/0073623 A1 (Drmanac et al) Apr. 17, 2013 (Apr. 17, 2013). Retrieved from the Internet: on Mar. 9, 2015 (Mar. 9, 2015). entire document.

SEQ ID No. 21806, US 2003/0194704 A1 (Penn et al) Oct. 16, 2003 (Oct. 16, 2003). Retrieved from the Internet: on Mar. 9, 2015 (Mar. 9, 2015). entire document.

* cited by examiner

Salv CKO; mdx-; utrn+/-

Salv CKO

Mouse Sav1 cDNA sequence:

ATGCTGTCCCGCAAGAAAACCAAAAACGAGGTGTCTAAGCCGGCCGAGGTGCAGGG
CAAGTACGTGAAGAAGGAGACGTCGCCCCTGCTGCGGAATCTCATGCCTTCATTCAT
TCGGCACGGTCCAACAATTCCCAGACGGACTGACCTCTGTCTTCCAGATTCAAGTGC
TACTGCTTTCTCAGCTTCTGGAGATGGTGTAGTTTCAAGAAACCAGAGTTTCCTGAGA
ACTGCAATTCAAAGGACACCTCATGAAGTAATGAGAAGAGAAAGCCACAGACTGTC
TGCCCCTTCTTACCTTGTCAGGAGCCTAGCAGATGTCCCTCGAGAGTGTGGCTCATCA
CAGTCATTTTTGACAGAAGTTAACTTTGCTGTTGAGAATGGAGACTCTGGCTCCCGAT
ACTTCTTCTCAGATAACTTTTTTGATGGACAGAGAAGGCGGCCACTTGGAGATCGTG
CACAAGAAGATTACAGATATTATGAATACAACCATGATCTCTTCCAGAGGATGCCAC
AGAGTCAGGGGAGGCACACTTCAGGTATTGGGAGAGTCACGGCTACATCTCTAGGG
AATTTAACTAACCATGGATCTGAAGATTTACCCCTTCCTCCTGGCTGGTCTGTGGACT
GGACAATGAGAGGGAGAAAATACTACATAGATCATAACACAAATACCACTCACTGG
AGTCATCCCCTTGAACGAGAAGGACTTCCTCCTGGCTGGGAACGAGTAGAGTCATCA
GAATTTGGAACCTATTACGTGGATCACACCAATAAAAGGGCTCAGTACAGGCACCCC
TGTGCTCCGAGTGTACCTCGGTATGATCAGCCTCCACCCATCACGTATCAGCCACAA
CAAACTGAAAGAAATCAGTCTCTCCTGGTCCCTGCAAATCCCTACCATACTGCAGAA
ATTCCTGACTGGCTTCAGGTTTATGCCCGAGCCCCTGTGAAATATGACCACATTCTGA
AGTGGGAGCTCTTCCAGCTGGCTGACCTGGACACGTACCAGGGAATGCTGAAGTTGC
TCTTCATGAAGGAACTGGAGCAGATTGTGAAGTTGTACGAGGCCTACAGACAGGCTC
TTCTCACTGAGTTGGAAAACCGCAAGCAGAGGCAGCAGTGGTATGCCCAGCAGCAT
GGCAAGACGTTCTTAAGTTAA

FIG. 6

Pig Sav1 cDNA sequence:

ATGCTGTCCCGAAAGAAAACCAAAAATGAAGTGTCCAAGCCGGCCGAGGTGCAGGG
GAAGTACGTGAAGAAGGAGACGTCGCCTCTGCTGCGGAATCTCATGCCTTCATTCAT
CCGGCACGGTCCCACAATTCCAAGACGAACTGATATCTGTCTTCCAGATTCCAGCTCT
AATGCCTTTTCAGCTTCTGGAGATGGAATAGTTTCAAGAAACCAGAGTTTCCTTAGA
ACTCCAATTCAAAGAACACCTCATGAAATAATGAGAAGAGAAAGCAACAGATTATC
TGCACCTTCTTATCTTGCCAGGAGTCTAGCAGATGTCCCTAGGGAATATGGCTCTTCT
CAGTCATTTTTAACAGAAGTTAATTTTGCTGTTGAAAATGGAGACTCTGGTTCCCGAT
ATTATTATTCCGATAATTATTTTGATGGTCAGAGGAGGCGCCAGCTTGGAGATCGCA
CACATGAAGACTATAGATATTATGACTACAACCACGATCTCTTCCAAAGAGTGCCAC
AAAATCAGGGGAGGCATGCTTCAGGTATTGGGAGAATTGCTGCTACATCTTTAGGAA
ATTTAACAAACCATGGTTCTGAAGATTTACCCCTTCCTCCTGGCTGGTCTGTGGACTG
GACAATGAGAGGGAGGAAATACTATATAGATCACAACACAAATACAACTCATTGGA
GCCATCCTCTTGAGCGAGAAGGACTTCCTCCAGGATGGGAGCGAGTTGAGTCATCAG
AATTTGGAACCTATTATGTAGATCACACAAATAAAAAGGCTCAATATAGGCATCCCT
GTGCTCCTAGCGTACCTCGATATGATCAACCTCCTCCTGTTACATACCAGCCACAGCA
AACTGAAAGAAATCAGTCCCTTCTGGTACCTGCAAATCCGTATCATGCTGCAGAAAT
TCCTGACTGGCTTCAGGTTTATGCTCGAGCCCCTGTGAAATATGACCACATTCTCAAG
TGGGAACTCTTCCAGCTGGCTGACCTGGATACATACCAGGGAATGCTGAAGTTGCTT
TTCATGAAAGAACTGGAACAGATTGTTAAAATGTATGAAGCCTACAGACAGGCTCTT
CTCACAGAGTTGGAAAATCGCAAGCAGAGACAACAGTGGTATGCCCAGCAACATGG
CAAGAATTTTTAA

FIG. 7

Human Sav1 cDNA sequence:

ATGCTGTCCCGAAAGAAAACCAAAAACGAAGTGTCCAAGCCGGCCGAGGTGCAGGG
GAAGTACGTGAAGAAGGAGACGTCGCCTCTGCTTCGGAATCTTATGCCTTCATTCAT
CCGGCATGGTCCAACAATTCCAAGACGAACTGATATCTGTCTTCCAGATTCAAGCCC
TAATGCCTTTTCAACTTCTGGAGATGTAGTTTCAAGAAACCAGAGTTTCCTTAGAACT
CCAATTCAAAGAACACCTCATGAAATAATGAGAAGAGAAAGCAACAGATTATCTGC
ACCTTCTTATCTTGCCAGAAGTCTAGCAGATGTCCCTAGAGAGTATGGTTCTTCTCAG
TCATTTGTAACGGAAGTTAGTTTTGCTGTTGAAAATGGAGACTCTGGTTCCCGATATT
ATTATTCAGACAATTTTTTTGATGGTCAGAGAAAGCGGCCACTTGGAGATCGTGCAC
ATGAAGACTACAGATATTATGAATACAACCATGATCTCTTCCAAAGAATGCCACAGA
ATCAGGGGAGGCATGCTTCAGGTATTGGGAGAGTTGCTGCTACATCTTTAGGAAATT
TGACTAACCATGGTTCTGAAGATTTACCCCTTCCTCCTGGCTGGTCTGTGGACTGGAC
AATGAGAGGGAGAAAATATTATATAGATCATAACACAAATACAACTCACTGGAGCC
ATCCTCTTGAGCGAGAAGGACTTCCTCCTGGATGGGAACGAGTTGAGTCATCCGAAT
TTGGAACCTATTATGTAGATCACACAAATAAGAAGGCCCAATACAGGCATCCCTGTG
CTCCTAGTGTACCTCGGTATGATCAACCACCTCCTGTCACATACCAGCCACAGCAAA
CTGAAAGAAATCAGTCCCTTCTGGTACCTGCAAATCCATATCATACTGCAGAAATTC
CTGACTGGCTTCAGGTTTACGCACGAGCCCCTGTGAAATATGACCACATTCTGAAGT
GGGAACTCTTCCAGCTGGCTGACCTGGATACATACCAGGGAATGCTAAAGTTGCTCT
TCATGAAAGAATTGGAGCAGATTGTTAAAATGTATGAAGCATACAGACAAGCCCTTC
TTACAGAGTTGGAAAACCGAAAGCAGAGACAGCAGTGGTATGCCCAACAACATGGA
AAAAATTTTTGA

FIG. 8

SEQUENCE LISTING

<160> NUMBER OF SEQ ID NOS: 12

<210> SEQ ID NO 1
<211> LENGTH: 1161
<212> TYPE: DNA
<213> ORGANISM: Mus musculus

<400> SEQUENCE: 1

```
atgctgtccc gcaagaaaac caaaaacgag gtgtctaagc cggccgaggt gcagggcaag     60

tacgtgaaga aggagacgtc gcccctgctg cggaatctca tgccttcatt cattcggcac    120

ggtccaacaa ttcccagacg gactgacctc tgtcttccag attcaagtgc tactgctttc    180

tcagcttctg gagatggtgt agtttcaaga aaccagagtt tcctgagaac tgcaattcaa    240

aggacacctc atgaagtaat gagaagagaa agccacagac tgtctgcccc ttcttacctt    300

gtcaggagcc tagcagatgt ccctcgagag tgtggctcat cacagtcatt tttgacagaa    360

gttaactttg ctgttgagaa tggagactct ggctcccgat acttcttctc agataacttt    420

tttgatggac agagaaggcg gccacttgga gatcgtgcac aagaagatta cagatattat    480

gaatacaacc atgatctctt ccagaggatg ccacagagtc aggggaggca cacttcaggt    540

attgggagag tcacggctac atctctaggg aatttaacta accatggatc tgaagattta    600

ccccttcctc ctggctggtc tgtggactgg acaatgagag ggagaaaata ctacatagat    660

cataacacaa ataccactca ctggagtcat ccccttgaac gagaaggact tcctcctggc    720

tgggaacgag tagagtcatc agaatttgga acctattacg tggatcacac caataaaagg    780

gctcagtaca ggcacccctg tgctccgagt gtacctcggt atgatcagcc tccacccatc    840

acgtatcagc cacaacaaac tgaaagaaat cagtctctcc tggtccctgc aaatccctac    900

catactgcag aaattcctga ctggcttcag gtttatgccc gagcccctgt gaaatatgac    960

cacattctga agtgggagct cttccagctg gctgacctgg acacgtacca gggaatgctg   1020

aagttgctct tcatgaagga actggagcag attgtgaagt tgtacgaggc ctacagacag   1080

gctcttctca ctgagttgga aaaccgcaag cagaggcagc agtggtatgc ccagcagcat   1140

ggcaagacgt tcttaagtta a                                             1161
```

<210> SEQ ID NO 2
<211> LENGTH: 1155
<212> TYPE: DNA
<213> ORGANISM: Sus scrofa

<400> SEQUENCE: 2

```
atgctgtccc gaaagaaaac caaaaatgaa gtgtccaagc cggccgaggt gcaggggaag     60

tacgtgaaga aggagacgtc gcctctgctg cggaatctca tgccttcatt catccggcac    120

ggtcccacaa ttccaagacg aactgatatc tgtcttccag attccagctc taatgccttt    180

tcagcttctg gagatggaat agtttcaaga aaccagagtt tccttagaac tccaattcaa    240

agaacacctc atgaaataat gagaagagaa agcaacagat tatctgcacc ttcttatctt    300

gccaggagtc tagcagatgt ccctagggaa tatggctctt ctcagtcatt tttaacagaa    360

gttaattttg ctgttgaaaa tggagactct ggttcccgat attattattc cgataattat    420

tttgatggtc agaggaggcg ccagcttgga gatcgcacac atgaagacta tagatattat    480

gactacaacc acgatctctt ccaaagagtg ccacaaaatc aggggaggca tgcttcaggt    540

attgggagaa ttgctgctac atctttagga aatttaacaa accatggttc tgaagattta    600

ccccttcctc ctggctggtc tgtggactgg acaatgagag ggaggaaata ctatatagat    660
```

```
cacaacacaa atacaactca ttggagccat cctcttgagc gagaaggact tcctccagga    720

tgggagcgag ttgagtcatc agaatttgga acctattatg tagatcacac aaataaaaag    780

gctcaatata ggcatccctg tgctcctagc gtacctcgat atgatcaacc tcctcctgtt    840

acataccagc cacagcaaac tgaaagaaat cagtcccttc tggtacctgc aaatccgtat    900

catgctgcag aaattcctga ctggcttcag gtttatgctc gagcccctgt gaaatatgac    960

cacattctca agtgggaact cttccagctg gctgacctgg atacatacca gggaatgctg   1020

aagttgcttt tcatgaaaga actggaacag attgttaaaa tgtatgaagc ctacagacag   1080

gctcttctca cagagttgga aaatcgcaag cagagacaac agtggtatgc ccagcaacat   1140

ggcaagaatt tttaa                                                    1155
```

<210> SEQ ID NO 3
<211> LENGTH: 1152
<212> TYPE: DNA
<213> ORGANISM: Homo sapiens

<400> SEQUENCE: 3

```
atgctgtccc gaaagaaaac caaaaacgaa gtgtccaagc cggccgaggt gcaggggaag     60

tacgtgaaga aggagacgtc gcctctgctt cggaatctta tgccttcatt catccggcat    120

ggtccaacaa ttccaagacg aactgatatc tgtcttccag attcaagccc taatgccttt    180

tcaacttctg gagatgtagt ttcaagaaac cagagtttcc ttagaactcc aattcaaaga    240

acacctcatg aaataatgag aagagaaagc aacagattat ctgcaccttc ttatcttgcc    300

agaagtctag cagatgtccc tagagagtat ggttcttctc agtcatttgt aacggaagtt    360

agttttgctg ttgaaaatgg agactctggt tcccgatatt attattcaga caattttttt    420

gatggtcaga gaaagcggcc acttggagat cgtgcacatg aagactacag atattatgaa    480

tacaaccatg atctcttcca aagaatgcca cagaatcagg ggaggcatgc ttcaggtatt    540

gggagagttg ctgctacatc tttaggaaat ttgactaacc atggttctga agatttaccc    600

cttcctcctg gctggtctgt ggactggaca atgagaggga gaaaatatta tatagatcat    660

aacacaaata caactcactg gagccatcct cttgagcgag aaggacttcc tcctggatgg    720

gaacgagttg agtcatccga atttggaacc tattatgtag atcacacaaa taagaaggcc    780

caatacaggc atccctgtgc tcctagtgta cctcggtatg atcaaccacc tcctgtcaca    840

taccagccac agcaaactga aagaaatcag tcccttctgg tacctgcaaa tccatatcat    900

actgcagaaa ttcctgactg gcttcaggtt tacgcacgag cccctgtgaa atatgaccac    960

attctgaagt gggaactctt ccagctggct gacctggata cataccaggg aatgctaaag   1020

ttgctcttca tgaaagaatt ggagcagatt gttaaaatgt atgaagcata cagacaagcc   1080

cttcttacag agttggaaaa ccgaaagcag agacagcagt ggtatgccca acaacatgga   1140

aaaaattttt ga                                                       1152
```

<210> SEQ ID NO 4
<211> LENGTH: 21
<212> TYPE: DNA
<213> ORGANISM: Mus musculus

<400> SEQUENCE: 4

```
aagtacgtga agaaggagac g                                               21
```

<210> SEQ ID NO 5

<211> LENGTH: 21
<212> TYPE: DNA
<213> ORGANISM: Mus musculus

<400> SEQUENCE: 5
aagatttacc ccttcctcct g 21

<210> SEQ ID NO 6
<211> LENGTH: 20
<212> TYPE: DNA
<213> ORGANISM: Mus musculus

<400> SEQUENCE: 6
attcctgact ggcttcaggt 20

<210> SEQ ID NO 7
<211> LENGTH: 21
<212> TYPE: DNA
<213> ORGANISM: Sus scrofa

<400> SEQUENCE: 7
aagtacgtga agaaggagac g 21

<210> SEQ ID NO 8
<211> LENGTH: 21
<212> TYPE: DNA
<213> ORGANISM: Sus scrofa

<400> SEQUENCE: 8
aagatttacc ccttcctcct g 21

<210> SEQ ID NO 9
<211> LENGTH: 20
<212> TYPE: DNA
<213> ORGANISM: Sus scrofa

<400> SEQUENCE: 9
attcctgact ggcttcaggt 20

<210> SEQ ID NO 10
<211> LENGTH: 21
<212> TYPE: DNA
<213> ORGANISM: Homo sapiens

<400> SEQUENCE: 10
aagtacgtga agaaggagac g 21

<210> SEQ ID NO 11
<211> LENGTH: 21
<212> TYPE: DNA
<213> ORGANISM: Homo sapiens

<400> SEQUENCE: 11
aagatttacc ccttcctcct g 21

<210> SEQ ID NO 12
<211> LENGTH: 20
<212> TYPE: DNA
<213> ORGANISM: Homo sapiens

<400> SEQUENCE: 12
attcctgact ggcttcaggt 20

HIPPO AND DYSTROPHIN COMPLEX SIGNALING IN CARDIOMYOCYTE RENEWAL

CROSS-REFERENCE TO RELATED APPLICATIONS

This application is a continuation of U.S. NonProvisional patent application Ser. No. 16/544,209 filed on Aug. 19, 2019, which is a continuation of U.S. NonProvisional patent application Ser. No. 16/164,550 filed on Oct. 18, 2018, which is a continuation of U.S. NonProvisional patent application Ser. No. 15/642,200 filed on Jul. 5, 2017 and registered as U.S. Pat. No. 10,119,141 on Nov. 6, 2018, which is a continuation of U.S. NonProvisional patent application Ser. No. 15/102,593 filed on Jun. 8, 2016 and registered as U.S. Pat. No. 9,732,345 on Aug. 15, 2017, which is a national phase application under 35 U.S.C. § 371 of International Application No. PCT/US2014/069349, filed Dec. 9, 2014, which claims priority to U.S. Provisional Patent Application Ser. No. 61/913,715, filed Dec. 9, 2013, the entire contents of each are incorporated by reference herein their entirety.

GOVERNMENT SUPPORT STATEMENT

This invention was made with government support under Grant HL007676 awarded by the National Institutes of Health. The government has certain rights in the invention.

TECHNICAL FIELD

The present disclosure concerns at least the fields of cell biology, molecular biology, and medicine.

BACKGROUND

Duchenne Muscular Dystrophy

Duchenne Muscular Dystrophy (DMD), a lethal inherited X-linked disorder occurring in 1 of every 3500 male births (Emery, 2002), is characterized by rapid and progressive degeneration of skeletal and cardiac muscle fibers. Importantly, DMD patients develop heart disease marked by myocardial necrosis, fibrosis and dilated cardiomyopathy. DMD arises from mutation of the dystrophin gene that encodes a 427 kd cytoskeletal protein present in skeletal, cardiac and smooth muscle cells (Hoffman et al., 1987; Hoffman et al., 1988). In DMD patients, dystrophin expression is abolished, leading to disruption of the dystrophin-associated glycoprotein complex (DGC), an essential membrane localized structure in skeletal and cardiac muscle (Ohlendieck and Campbell, 1991; Ohlendieck et al., 1993). A valuable mouse model for DMD is the mdx mouse, a dystrophin-null strain that exhibits a disease phenotype with similarity to human DMD (Bulfield et al., 1984). Although much less severe than human DMD, the mdx mice have characteristics of the human disease such as skeletal muscle degeneration/regeneration and cardiomyopathy after aging.

Introduction to Hippo-Signaling

The mammalian core Hippo-signaling components include the Ste20 kinases Mst1 and Mst2 that are orthologous to the *Drosophila* Hippo kinase. Mst kinases, when complexed with the Salvador (Salv) scaffold protein, phosphorylate the Large Tumor Suppressor Homolog (Lats) kinases. Mammalian Lats1 and Lats2 are NDR family kinases and are orthologous to *Drosophila* Warts. Lats kinases, in turn, phosphorylate Yap and Taz, two related transcriptional co-activators that are the most downstream Hippo-signaling components and partner with transcription factors such as Tead to regulate gene expression. Yap also interacts with β-catenin, an effector of canonical Wnt signaling to regulate gene expression. Upon phosphorylation, Yap and Taz are excluded from the nucleus and rendered transcriptionally inactive (FIG. 1).

Previous cardiac loss-of-function studies in mice revealed that Hippo-signaling inhibits cardiomyocyte proliferation to control heart size (Heallen et al., 2011). Salv deficient hearts develop cardiomegaly with a 2.5-fold increase in heart size due to cardiomyocyte hyperplasia. Additionally, experiments investigating Yap in cardiomyocyte development support the conclusion that Yap is the major Hippo effector molecule during cardiomyocyte development (von Gise et al., 2012; Xin et al., 2011). Yap is a cofactor that partners with DNA binding transcriptional regulators. The current literature indicates that Tead-family co factors are primary Yap partners (Halder and Johnson, 2011).

The present disclosure concerns methods and compositions that address a long-felt need in the art to provide therapy for cardiac conditions, including at least DMD, by targeting the Hippo pathway.

BRIEF SUMMARY

The present invention is directed to methods and compositions that provide therapy for at least one medical condition that directly or indirectly affects cardiac muscle cells (cardiomyocytes) in a mammalian individual, including humans, dogs, cats, horses, pigs, and so forth. The medical condition may be of any kind, including a cardiac condition such as heart failure, cardiomyopathy, myocardial infarction, and so forth. The medical condition may have a cardiac condition as its primary symptom or cause or it may be a secondary symptom or cause. The individual may be male or female and may be of any age.

In particular embodiments, an individual in need of therapy for a cardiac medical condition is provided an effective amount of one or more nucleic acids, or cells comprising one or more nucleic acids, in which the nucleic acids provide therapeutic benefit to the individual. In specific embodiments, the nucleic acid is a form that directly or indirectly provides RNA interference, including at least shRNA. In particular embodiments, the shRNA composition targets a member of the Hippo pathway. Although it may target any member of the Hippo pathway, in specific embodiments, the shRNA targets Salvador (Sav1).

In embodiments of the disclosure, there are nucleic acid compositions that target Sav1 of a mammal, and in specific embodiments the nucleic acid compositions are shRNA molecules. In specific embodiments, there are therapeutic compositions that comprise shRNA molecules comprising one or more of SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. The compositions may or may not be encompassed in a vector, including a viral vector or non-viral vector. In particular embodiments, the shRNA sequences are utilized in a non-integrating vector.

SUMMARY

In some embodiments, there is an isolated synthetic nucleic acid composition, comprising SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12 and/or a derivative nucleic acid comprising at least 80% identity to one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. The derivative nucleic acid may be at least 85%, 90%, 95%, 96%, 97%, 98%, or 99% identical to one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

In certain embodiments, the nucleic acid comprises the sequence of SEQ ID NO:4 (or SEQ ID NO:5, 6, 7, 8, 9, 10, 11, or 12) and further comprises an antisense sequence of SEQ ID NO:4 (or, respectively, SEQ ID NO:5, 6, 7, 8, 9, 10, 11, or 12), wherein when the sequence and the antisense sequence are hybridized together to form a duplex structure, the sequence and the antisense sequence are separated by a loop structure.

In specific embodiments, the nucleic acid is at least 43 nucleotides in length or no more than 137 nucleotides in length. In some embodiments, the loop structure is between 5 and 19 nucleotides in length. In particular embodiments, the derivative nucleic acid has 1, 2, 3, 4, or 5 mismatches compared to the respective SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

In some embodiments of the composition, the nucleic acid or derivative nucleic acid is comprised in a vector, such as a viral vector or a non-viral vector. The vector may be a non-integrating vector. The vector may be a non-integrating vector that is a lentiviral vector. In some embodiments of the vector, two or more of nucleic acids comprising SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12 are present on the same vector.

In specific embodiments, the expression of the nucleic acid is regulated by a tissue-specific or cell-specific promoter, such as a cardiomyocyte-specific promoter, for example the rat ventricle-specific cardiac myosin light chain 2 (MLC-2v) promoter; cardiac muscle-specific alpha myosin heavy chain (MHC) gene promoter; cardiac cell-specific minimum promoter from −137 to +85 of NCX1 promoter; chicken cardiac troponin T (cTNT), or a combination thereof.

In certain embodiments, two or more of nucleic acids comprising SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12 are present on the same vector. In specific cases, two or more nucleic acids are regulated by the same regulatory sequence or are regulated by a different regulatory sequence.

In one embodiment, there is a method of treating an individual for a cardiac condition, comprising the step of providing an effective amount of a composition encompassed by the disclosure to the individual. In certain embodiments, the cardiac condition in the individual causes the individual to be in need of cardiomyocyte renewal. In certain embodiments, the heart of the individual has cardiomyocyte apoptosis, necrosis, and/or autophagy. In specific embodiments, the cardiac condition comprises cardiovascular disease, cardiomyopathy, heart failure, myocardial infarction, ischemia, necrosis, fibrosis, or diabetic cardiomyopathy, age-related cardiomyopathy. In particular embodiments, the individual has Duchenne muscular dystrophy. The composition may be provided to the individual more than once. The composition may be provided to the individual systemically or locally. In a specific embodiment, the individual is provided an additional therapy for the cardiac condition.

In certain embodiments, there is a kit comprising a composition as encompassed by the disclosure, wherein the composition is housed in a suitable container.

In particular embodiments, there is a method of treating a cardiac condition in an individual, comprising the step of providing to the individual a therapeutically effective amount of a shRNA that targets Salvador (Sav1). In a specific embodiment, the shRNA is provided to the individual in the AAV9 vector. In particular cases, the individual has Duchenne muscular dystrophy.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 6 illustrates the mouse Sav1 cDNA sequence (SEQ ID NO:1). The grayed regions demonstrate examples of shRNA sequences (SEQ ID NO:4, SEQ ID NO:5, and SEQ ID NO:6, respectively). Alternating exons are show by sequences that are double-underlined vs. sequences that are not double-underlined. Protein structural domains are shown by sequences that are single underlined, in order of 5' to 3'; WW domain, WW domain, SARAH domain.

FIG. 7 illustrates the pig Sav1 cDNA sequence (SEQ ID NO:2). The grayed regions demonstrate examples of shRNA sequences (SEQ ID NO:7, SEQ ID NO:8, and SEQ ID NO:9, respectively). Alternating exons are show by sequences that are double-underlined vs. sequences that are not double-underlined. Protein structural domains are shown by sequences that are single underlined, in order of 5' to 3'; WW domain, WW domain, SARAH domain; and FIG. 8 illustrates the human Sav1 cDNA sequence (SEQ ID NO:3). The grayed regions demonstrate examples of shRNA sequences (SEQ ID NO:10, SEQ ID NO:11, and SEQ ID NO:12, respectively). Alternating exons are show by sequences that are double-underlined vs. sequences that are not double-underlined. Protein structural domains are shown by sequences that are single underlined, in order of 5' to 3'; WW domain, WW domain, SARAH domain.

DETAILED DESCRIPTION

I. Exemplary Definitions

Figure 1:
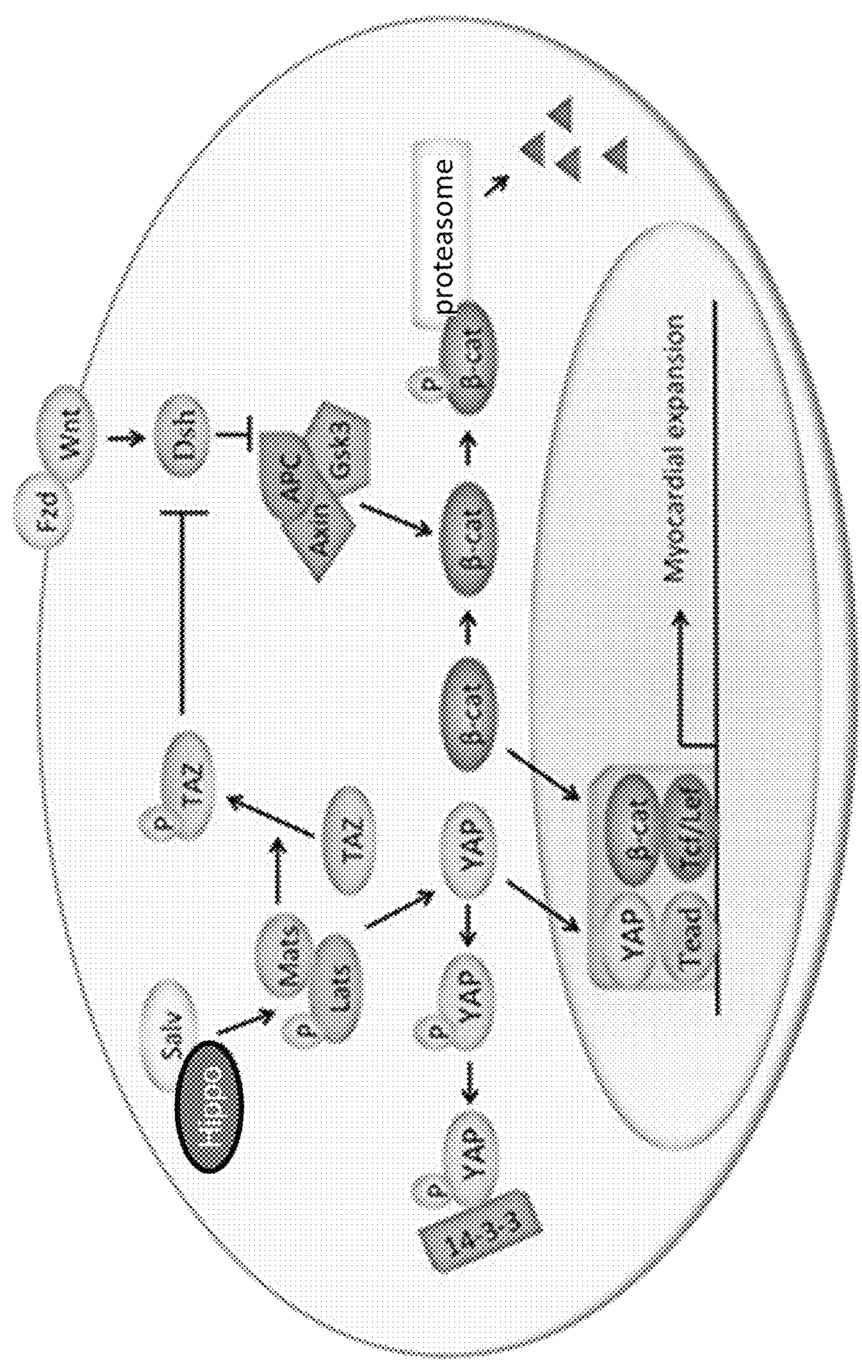
FIG. 1 illustrates an example of a model for Hippo signaling during development and regeneration.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "complementary nucleotide sequence," also known as an "antisense sequence," refers to a sequence of a nucleic acid that is completely complementary to the sequence of a "sense" nucleic acid encoding a protein (e.g., complementary to the coding strand of a double-stranded cDNA molecule or complementary to an mRNA sequence). Herein, nucleic acid molecules are provided that comprise a sequence complementary to at least about 15, 16, 17, 18, 19, 20, 21, 22, 23, 24, or 25 nucleotides.

As used herein, the term "correspond to a nucleotide sequence" refers to a nucleotide sequence of a nucleic acid encoding an identical sequence. In some instances, when antisense nucleotides (nucleic acids) or siRNA's (small inhibitory RNA) (processed from the shRNA) bind to a target sequence a particular antisense or small inhibitory RNA (siRNA) sequence is substantially complementary to the target sequence, and thus will specifically bind to a portion of an mRNA encoding polypeptide. As such, typically the sequences of those nucleic acids will be highly complementary to the mRNA target sequence, and will have no more than 1, 2, 3, 4, 5, 6, 7, 8, 9, or 10 base mismatches throughout the sequence. In many instances, it may be desirable for the sequences of the nucleic acids to be exact matches, i.e. be completely complementary to the sequence to which the oligonucleotide specifically binds, and therefore have zero mismatches along the complementary stretch. Highly complementary sequences will typically bind quite specifically to the target sequence region of the mRNA and will therefore be highly efficient in reducing, and/or even inhibiting the translation of the target mRNA sequence into polypeptide product. See, for example, U.S. Pat. No. 7,416,849.

Substantially complementary oligonucleotide sequences will be greater than about 80 percent complementary (or '% exact-match') to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to the target mRNA to which the designed oligonucleotide specifically binds. See, for example, U.S. Pat. No. 7,416,849. Percent similarity or percent complementary of any nucleic acid sequence may be determined, for example, by utilizing any computer programs known in the art.

As used herein, the term "knock-down" or "knock-down technology" refers to a technique of gene silencing in which the expression of a target gene or gene of interest is reduced as compared to the gene expression prior to the introduction of the shRNA, which can lead to the inhibition of production of the target gene product. The term "reduced" is used herein to indicate that the target gene expression is lowered by 0.1-100%. For example, the expression may be reduced by 0.5, 1, 5, 10, 15, 20, 25, 30, 35, 40, 45, 50, 55, 60, 65, 70, 75, 80, 85, 90, 95, or even 99%. The expression may be reduced by any amount (%) within those intervals, such as for example, 2-4, 11-14, 16-19, 21-24, 26-29, 31-34, 36-39, 41-44, 46-49, 51-54, 56-59, 61-64, 66-69, 71-74, 76-79, 81-84, 86-89, 91-94, 96, 97, 98 or 99. Knock-down of gene expression can be directed by the use of siRNAs or shRNAs.

As used herein, the term "nucleotide sequence" refers to a polymer of DNA or RNA which can be single-stranded or double-stranded, optionally containing synthetic, non-natural or altered nucleotide bases capable of incorporation into DNA or RNA polymers. The term "polynucleotide" is used interchangeably with the term "oligonucleotide." The term "nucleotide sequence" is interchangeable with "nucleic acid sequence" unless otherwise clearly stated. "Nucleotide sequence" and "nucleic acid sequence" are terms referring to a sequence of nucleotides in a polynucleotide molecule.

As used herein, the term "operably-linked" refers to the association of nucleic acid sequences on a polynucleotide so that the function of one of the sequences is affected by another. For example, a regulatory DNA sequence is said to be "operably linked to" a DNA sequence that codes for an RNA ("an RNA coding sequence" or "shRNA encoding sequence") or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. An RNA coding sequence refers to a nucleic acid that can serve as a template for synthesis of an RNA molecule such as an siRNA and an shRNA. Preferably, the RNA coding region is a DNA sequence.

As used herein, the term "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion or as described elsewhere throughout the specification.

As used herein, the term "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that stimulates promoter activity and may be an innate element of the promoter or a heterologous element inserted to enhance the level or tissue specificity of a promoter. It is capable of operating in both orientations (sense or antisense), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Any promoter known in the art which regulates the expression of the shRNA or RNA coding sequence is envisioned in the practice of the invention.

As used herein, the term "reporter element" or "marker" is meant a polynucleotide that encodes a polypeptide capable of being detected in a screening assay. Examples of polypeptides encoded by reporter elements include, but are not limited to, lacZ, GFP, luciferase, and chloramphenicol acetyltransferase. See, for example, U.S. Pat. No. 7,416,849. Many reporter elements and marker genes are known in the art and envisioned for use in the inventions disclosed herein.

As used herein, the term "RNA transcript" refers to the product resulting from RNA polymerase catalyzed transcription of a DNA sequence. "Messenger RNA transcript (mRNA)" refers to the RNA that is without introns and that can be translated into protein by the cell.

As used herein, the terms "small interfering" or "short interfering RNA" or "siRNA" refer to an RNA duplex of nucleotides that is targeted to a desired gene and is capable of inhibiting the expression of a gene with which it shares homology. The RNA duplex comprises two complementary single-stranded RNAs of 15, 16, 17, 18, 19, 20, 21, 22, 23, 24, or 25 nucleotides that form 15, 16, 17, 18, 19, 20, 21, 22, 23, 24, or 25 base pairs and possess 3' overhangs of two nucleotides. The RNA duplex is formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. The duplex can be 29, 28, 27, 26, 25, 24, 23, 22, 21, 20, 19, 18, 17, 16, 15, 14, 13, 12, 11 or 10 nucleotides in length. The length of the duplex can be 17-25 nucleotides in length. The duplex RNA can be expressed in a cell from a single construct.

As used herein, the term "shRNA" (small hairpin RNA) refers to an RNA duplex wherein a portion of the siRNA is part of a hairpin structure (shRNA). In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some aspects, the overhang is a 3' or a 5' overhang 0, 1, 2, 3, 4 or 5 nucleotides in length. In one aspect of this invention, a nucleotide sequence in the vector serves as a template for the expression of a small hairpin RNA, comprising a sense region, a loop region and an antisense region. Following expression the sense and antisense regions form a duplex. It is this duplex, forming the shRNA, which hybridizes to, for example, the Sav1 mRNA and reduces expression of Sav1.

As used herein, the term "treating" refers to ameliorating at least one symptom of, curing and/or preventing the development of a disease or disorder such as for example, but not limited to, ischemic heart disease, heart failure, cardiomyopathy, etc.

As used herein, the term "vector" refers to any viral or non-viral vector, as well as any plasmid, cosmid, phage or binary vector in double or single stranded linear or circular form that may or may not be self-transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this invention.

II. General Embodiments

Embodiments of the disclosure concern methods and compositions for treatment of cardiac medical conditions, including those in which cardiomyocytes are in need of being renewed. The cardiomyocytes may be in need of renewal for any reason, including for disease, underlying genetic condition, and/or trauma, for example. In specific embodiments, the individual has cardiomyocyte injury, necrosis, and/or fibrosis of the heart, such as with Duchenne muscular dystrophy (DMD), for example.

In specific embodiments, methods and compositions are employed for an individual with DMD. The diseased heart in DMD patients has widespread cardiomyocyte injury, necrosis and fibrosis. Similarly, mdx mutant mice that model human DMD have cardiomyopathy with heart failure and severe fibrosis and dilation. The Hippo signaling pathway was identified as a critical repressor of cardiac regeneration following tissue amputation or myocardial infarction (Heallen et al., 2013). In addition, data indicate that Hippo regulates transcription of DMD-related genes in the heart. Taken together, it was considered that Hippo signaling inhibits a repair response to Duchenne cardiomyopathy. As shown herein, neonatal mdx hearts fail to regenerate following apex resection, in contrast to regenerative wild-type neonate hearts. Most notably, this regenerative capacity was largely restored in Hippo; mdx compound mutant hearts, indicating genetic suppression of the mdx heart phenotype. Taken together, modulating Hippo signaling serves as a powerful approach to repair heart muscle, such as DMD heart muscle.

In addition to improving DMD cardiomyopathy, it is shown herein that Hippo pathway inhibition after established heart failure (HF) drastically improved cardiac function in a mouse model of ischemic cardiomyopathy and HF. Mice with established ischemic cardiomyopathy and HF were generated by waiting three weeks after induction of a myocardial infarct to deplete the Hippo pathway. At the three-week time point, the Hippo pathway was inactivated and cardiac function was followed at two-week intervals by echocardiography. Hippo deficiency strongly enhances cardiac repair in the context of established HF such that Hippo mutants recover function equal to that of un-operated sham controls.

There is demonstrated herein a unique, but exemplary, set of three short hairpin RNAs (shRNA) that specifically target the Hippo pathway member Salvador (Sav1). The shRNAs provide selective reduction in Sav1 mRNA levels similar to a genetic knockout in a mouse model. In specific embodiments, the shRNAs can be delivered using an AAV9 (Adeno Associated Virus serotype 9) vector that has tropism for the heart. Particular embodiments of the disclosure contemplate the shRNA sequence of nucleotides specific to target Sav1.

III. Salvador

In particular embodiments, the Hippo pathway member Salvador (salvador family WW domain containing protein 1) is targeted with shRNA in treatments for cardiac medical conditions. The gene may be referred to as salvador homolog 1, Salv, SAV1, SAV, WW45, or WWP4. A representative nucleic acid is provided at GenBank® Accession No. CR457297.1, and a representative protein sequence is provided at GenBank® Accession No. Q9H4B6.

The gene encodes a protein which includes 2 WW domains (a modular protein domain that mediates specific interactions with protein ligands) and a coiled-coil region. It is ubiquitously expressed in adult tissues. It also includes a SARAH (Sav/Rassf/Hpo) domain at the C terminus (three classes of eukaryotic tumor suppressors that give the domain its name) In the Say (Salvador) and Hpo (Hippo) families, the SARAH domain mediates signal transduction from Hpo via the Say scaffolding protein to the downstream component Wts (Warts); the phosphorylation of Wts by Hpo triggers cell cycle arrest and apoptosis by down-regulating cyclin E, Diap 1 and other targets. The SARAH domain may also be involved in dimerization.

IV. Examples of/Methods of Treatment

In embodiments of the disclosure, there are methods of treating an individual with a cardiac condition using nucleic acids that target the Sav1 gene. In specific embodiments, the cardiac condition includes cardiomyocytes that are in need of renewal either because of disease (contracted or genetic, for example) or because of trauma, for example. In specific embodiments, there is diseased heart in the individual. The individual may have cardiomyocytes that are in need of renewal for any reason. Cardiomyocytes in the individual may be apoptotic, autophagic, or the tissue may be necrotic, for example.

In specific embodiments, the individual may have heart failure, fibrosis of the heart, cardiomyopathy, ischemic cardiomyopathy, myocardial necrosis, dilated cardiomyopathy, degeneration of skeletal and/or cardiac muscle fibers, Diabetic cardiomyopathy, age-related cardiomyopathy, and so forth. In specific embodiments, methods of the disclosure allow for the ability of cardiomyocytes to re-enter the cell cycle. The individual may be in need of improved cardiac function for any reason, including because of age, disease, trauma, and so forth.

In particular embodiments, the individual is provided an effective amount of nucleic acid that targets Sav1 such that existing cardiomyocytes in the individual are able to renew. In other embodiments, an individual is provided nucleic acids that target Sav1 wherein the nucleic acids are already present in a cell at the time of delivery, including a cardiomyocyte or stem cell, for example.

The nucleic acid compositions of the disclosure may be provided to the individual once or more than once. The delivery may occur upon the diagnosis of a need for cardiomyocyte renewal or upon diagnosis of a cardiac condition. Delivery may occur to an individual who is susceptible to a cardiac condition, such as having a personal or family history, being overweight, having high cholesterol, and/or a smoker. The delivery may cease or continue once it is determined that a cardiac symptom is improved and/or that cardiomyocytes are being renewed.

V. Nucleic Acids that Target Sav1

In particular embodiments, there are one or more nucleic acids that target Sav1 such that expression of Sav1 is detectably reduced. The nucleic acids may be DNA or RNA, but in specific embodiments the nucleic acids are RNA, such as shRNA.

In one embodiment, the shRNA is a "hairpin" or stem-loop RNA molecule, comprising a sense region, a loop region and an antisense region complementary to the sense region. In other embodiments the shRNA comprises two distinct RNA molecules that are non-covalently associated to form a duplex. See, for example, U.S. Pat. No. 7,195,916.

In particular cases, shRNA is a single-stranded RNA molecule that forms a stem-loop structure in vivo, and it may be from about 40 to 135 nucleotides in length. In at least certain cases, a 5- to 19-nucleotide loop connects the two complementary 19- to 29-nucleotide-long RNA fragments that create the double-stranded stem by base pairing. Transcription and synthesis of shRNA in vivo is directed by Pol III promoter, and then the resulting shRNA is cleaved by Dicer, an RNase III enzyme, to generate mature siRNA. The mature siRNA enters the RISC complex. Thus, in specific embodiments, shRNA for inhibition of Sav1 expression in accordance with the present disclosure contains both sense and antisense nucleotide sequences.

Although the present disclosure provides specific examples of Sav1-targeting shRNAs (SEQ ID NO:4, 5, 6, 7, 8, 9, 10, 11, or 12), other shRNA compositions may be employed. Those of skill in the art may identify appropriate sequences in any manner, but in specific embodiments one can align the gene from two or more organisms, scan overlapping regions for the amino acid-encoding sequence, review the sequence for regions of a certain length (such as, for example 19 nt), review the sequence for those having no more than 3 nt repeats, and/or blast potential sequences to ensure there is <15 bp homology to any other part of the human genome.

When appropriately targeted via its nucleotide sequence to a specific mRNA in cells, the shRNA specifically suppress gene expression of Sav1. In at least some cases, shRNAs can reduce the cellular level of specific mRNAs, and decrease the level of proteins coded by such mRNAs. shRNAs utilize sequence complementarity to target an mRNA for destruction, and are sequence-specific. Thus, they can be highly target-specific, and in mammals have been shown to target mRNAs encoded by different alleles of the same gene.

In specific embodiments, an shRNA corresponding to a region of a target gene to be down-regulated or knocked-down is expressed in the cell. The shRNA duplex may be substantially identical (for example, at least about 80%, 81%, 82%, 83%, 84%, 85%, 86%, 87%, 88%, 89%, 90%, 91%, 92%, 93%, 94%, 95%, 96%, 97%, 98%, or 99% identical) in sequence to the sequence of the gene targeted for down regulation. In specific embodiments, there are no more than 5 mismatches between the sequence of the shRNA and the target Sav1 sequence. In specific embodiments, a minimum of 18 bp homology is utilized for the region of complementarity between the shRNA sequence and its target. In particular embodiments, specific assays are utilized to test suitable mismatches for the shRNA and its target. In certain embodiments, an algorithm may be employed to identify suitable mismatches for the shRNA and its target.

Thus, it should be noted that full complementarity between the target sequence and the shRNA is not required. That is, the resultant antisense siRNA (following processing of the shRNA) is sufficiently complementary with the target sequence. The sense strand is substantially complementary with the antisense strand to anneal (hybridize) to the antisense strand under biological conditions.

In particular, the complementary polynucleotide sequence of shRNA can be designed to specifically hybridize to a particular region of a desired target protein or mRNA to interfere with replication, transcription, or translation. The term "hybridize" or variations thereof, refers to a sufficient degree of complementarity or pairing between an antisense nucleotide sequence and a target DNA or mRNA such that stable and specific binding occurs there between. In particular, 100% complementarity or pairing is desirable but not required. Specific hybridization occurs when sufficient hybridization occurs between the antisense nucleotide sequence and its intended target nucleic acids in the substantial absence of non-specific binding of the antisense nucleotide sequence to non-target sequences under predetermined conditions, e.g., for purposes of in vivo treatment, preferably under physiological conditions. Preferably, specific hybridization results in the interference with normal expression of the gene product encoded by the target DNA or mRNA.

For example, an antisense nucleotide sequence can be designed to specifically hybridize to the replication or transcription regulatory regions of a target gene, or the translation regulatory regions such as translation initiation region and exon/intron junctions, or the coding regions of a target mRNA. In specific embodiments, the shRNA targets a sequence that encodes the N-terminal region of the Sav1 protein, sequence that encodes the middle of the Sav1 protein, or sequence that encodes the C-terminal region of the Sav1 protein.

shRNA: Synthesis

As is generally known in the art, commonly used oligonucleotides are oligomers or polymers of ribonucleic acid or deoxyribonucleic acid having a combination of naturally-occurring purine and pyrimidine bases, sugars and covalent linkages between nucleosides including a phosphate group in a phosphodiester linkage. However, it is noted that the term "oligonucleotides" also encompasses various non-naturally occurring mimetics and derivatives, i.e., modified forms, of naturally-occurring oligonucleotides as described below.

shRNA molecules of the disclosure can be prepared by any method known in the art for the synthesis of DNA and RNA molecules. These include techniques for chemically synthesizing oligodeoxy-ribonucleotides and oligo-ribonucleotides well known in the art such as, for example, solid phase phosphoramidite chemical synthesis. Alternatively, RNA molecules can be generated by in vitro and in vivo transcription of DNA sequences encoding the shRNA molecule. Such DNA sequences may be incorporated into a wide variety of vectors that incorporate suitable RNA polymerase promoters such as the T7 or SP6 polymerase promoters. Alternatively, antisense cDNA constructs that synthesize shRNA constitutively or inducibly, depending on the promoter used, can be introduced stably into cell lines.

shRNA molecules can be chemically synthesized using appropriately protected ribonucleoside phosphoramidites and a conventional DNA/RNA synthesizer. Custom shRNA synthesis services are available from commercial vendors such as Ambion (Austin, Tex., USA) and Dharmacon Research (Lafayette, Colo., USA). See, for example, U.S. Pat. No. 7,410,944.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone. An antisense nucleic acid of the invention can be constructed using chemical synthesis or enzymatic ligation reactions using procedures known in the art. An antisense oligonucleotide can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

The shRNA molecules of the invention can be various modified equivalents of the structures of any Sav1 shRNA. A "modified equivalent" means a modified form of a particular siRNA molecule having the same target-specificity (i.e., recognizing the same mRNA molecules that complement the unmodified particular siRNA molecule). Thus, a modified equivalent of an unmodified siRNA molecule can have modified ribonucleotides, that is, ribonucleotides that contain a modification in the chemical structure of an unmodified nucleotide base, sugar and/or phosphate (or phosphodiester linkage). See, for example, U.S. Pat. No. 7,410,944.

Preferably, modified shRNA molecules contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like. See, for example, U.S. Pat. No. 7,410,944.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See, for example, U.S. Pat. No. 7,410,944.

Examples of the non-phosphorous containing backbones described above are known in the art, e.g., U.S. Pat. No. 5,677,439, each of which is herein incorporated by reference. See, for example, U.S. Pat. No. 7,410,944.

Modified forms of shRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxy methyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyl uridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and 0-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyl adenosine, beta-D-mannosylqueosine, uridine-5-oxyacetic acid, 2-thiocytidine, threonine derivatives, and the like. See, for example, U.S. Pat. No. 7,410,944.

In addition, modified shRNA compounds can also have substituted or modified sugar moieties, e.g., 2'-O-methoxyethyl sugar moieties. See, for example, U.S. Pat. No. 7,410,944.

Additionally, to assist in the design of shRNAs for the efficient silencing of any target gene, several supply companies maintain web-based design tools that utilize these general guidelines for "picking" shRNAs when presented with the mRNA or coding DNA sequence of the target gene. Examples of such tools can be found at the web sites of Dharmacon, Inc. (Lafayette, Colo.), Ambion, Inc. (Austin, Tex.). As an example, selecting shRNAs involves choosing a site/sequence unique to the target gene (i.e., sequences that share no significant homology with genes other than the one being targeted), so that other genes are not inadvertently targeted by the same shRNA designed for this particular target sequence.

Another criterion to be considered is whether or not the target sequence includes a known polymorphic site. If so, shRNAs designed to target one particular allele may not effectively target another allele, since single base mismatches between the target sequence and its complementary strand in a given shRNA can greatly reduce the effectiveness of RNAi induced by that shRNA. Given that target sequence and such design tools and design criteria, an ordinarily skilled artisan apprised of the present disclosure should be able to design and synthesized additional siRNA compounds useful in reducing the mRNA level of Sav1.

shRNA: Administration

The present disclosure provides a composition of a polymer or excipient and one or more vectors encoding one or more shRNA molecules. The vector can be formulated into a pharmaceutical composition with suitable carriers and administered into a mammal using any suitable route of administration.

Because of this precision, side effects typically associated with traditional drugs can be reduced or eliminated. In addition, shRNA are relatively stable and, like antisense, they can also be modified to achieve improved pharmaceutical characteristics, such as increased stability, deliverability, and ease of manufacture. Moreover, because shRNA molecules take advantage of a natural cellular pathway, i.e., RNA interference, they are highly efficient in destroying targeted mRNA molecules. As a result, it is relatively easy to achieve a therapeutically effective concentration of an shRNA compound in a subject. See, for example, U.S. Pat. No. 7,410,944.

shRNA compounds may be administered to mammals by various methods through different routes. They can also be delivered directly to a particular organ or tissue by any suitable localized administration methods such as direct injection into a target tissue. Alternatively, they may be delivered encapsulated in liposomes, by iontophoresis, or by incorporation into other vehicles such as hydrogels, cyclodextrins, biodegradable nanocapsules, and bioadhesive microspheres.

In vivo inhibition of specific gene expression by RNAi injected intravenously has been achieved in various organisms including mammals. In particular embodiments, the shRNA molecules are comprised in a vector, including a viral or non-viral vector. In specific embodiments, the vector is non-integrating, although in other embodiments it is integrating. Viral vectors may be lentiviral, adenoviral, adeno-associated viral, and retroviral, for example. Non-viral vectors include plasmids. In specific embodiments, the AAV9 vector (Piras et al., 2013) is employed. Vectors may be delivered to an individual systemically or locally. In certain embodiments, the vectors utilize tissue-specific or cell-specific promoters, such as cardiomyocyte-specific promoters. In specific embodiments, the vectors are delivered by local injection.

One route of administration of shRNA molecules of the invention includes direct injection of the vector at a desired tissue site, such as for example, into diseased cardiac tissue or into ischemic heart tissue.

In general, included in the invention is a vector comprising a polynucleotide sequence, and a promoter operably-linked to an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment. The second segment, located immediately 3' of the first segment, encodes a loop structure containing from 4-10 nucleotides (i.e., 4, 5, 6, 7, 8, 9, 10). The nucleic acid sequence is expressed as an siRNA and functions as a small hairpin RNA molecule (shRNA) targeted against a designated nucleic acid sequence.

More specifically, the present invention includes compositions and methods for selectively reducing the expression of the gene product from Sav1. The present invention provides a vector comprising a polynucleotide sequence which comprises a nucleic acid sequence encoding a shRNA targeted against Sav1. The shRNA forms a hairpin structure comprising a duplex structure and a loop structure. The loop structure may contain from 4 to 10 nucleotides, such as 4, 5 or 6 nucleotides. The duplex is less than 30 nucleotides in length, such as from 10 to 27 nucleotides. The shRNA may further comprise an overhang region. Such an overhang may be a 3' overhang region or a 5' overhang region. The overhang region may be, for example, 1, 2, 3, 4, 5, or 6 nucleotides in length.

The invention provides, inter alia, a method of treating a mammal by administering to the mammal a composition comprising one or more vectors described herein. In one aspect of the invention, multiple vectors each encoding a different shRNA (targeted to a different region of the Sav1 nucleic acid sequence) may be administered simultaneously or consecutively to the mammal. An individual vector may encode multiple shRNAs targeted to different areas of the same gene; i.e., comprising two or more of a shRNA comprising SEQ ID NO: 10 and shRNA comprising SEQ ID NO: 11 and a shRNA comprising SEQ ID NO: 12. In another aspect, an individual vector may encode multiple copies of shRNA comprising SEQ ID NO: 10 or multiple copies of shRNA comprising SEQ ID NO: 11 or multiple copies of shRNA comprising SEQ ID NO: 12, in any ratio.

The vector of the invention may further comprise a promoter. Examples of promoters include regulatable promoters and constitutive promoters. For example, the promoter may be a CMV or RSV promoter. The vector may further comprise a polyadenylation signal, such as a synthetic minimal polyadenylation signal. Many such promoters are known in the art and are envisioned for use in this invention. In other instances, the promoter may be a tissue specific promoter, such as a cardiac tissue specific promoter.

The vector may further comprise one or more marker genes or reporter genes. Many marker genes and reporter genes are known in the art. The present invention contemplates use of one or more marker genes and/or reporter genes known in the art in the practice of the invention. The marker genes or reporter genes provide a method to track expression of one or more linked genes. The marker genes or reporter genes upon expression within the cell, provide products, usually proteins, detectable by spectroscopic, photochemical, biochemical, immunochemical, chemical, or other physical means. Gene expression products, whether from the gene of interest, marker genes or reporter genes may also be detected by labeling. Labels envisioned for use in the inventions included herein include, but are not limited to, fluorescent dyes, electron-dense reagents, enzymes (for example, as commonly used in an ELISA), biotin, digoxigenin, or haptens and proteins which can be made detectable, e.g., by incorporating a radiolabel into the peptide or used to detect antibodies specifically reactive with the peptide. See, for example, U.S. Pat. No. 7,419,779.

In one aspect of the invention, one or more vectors comprising one or more of shRNA of the invention can be re-administered an unlimited number of times after a first administration at any time interval or intervals after the first administration.

shRNA: Pharmaceutical Compositions

The shRNA encoding nucleic acids of the present invention can be formulated in pharmaceutical compositions, which are prepared according to conventional pharmaceutical compounding techniques. See, e.g., Remington's Pharmaceutical Sciences, 18th Ed. (1990, Mack Publishing Co., Easton, Pa.). The pharmaceutical compositions of the invention comprise a therapeutically effective amount of the vector encoding shRNA. These compositions can comprise, in addition to the vector, a pharmaceutically acceptable excipient, carrier, buffer, stabilizer or other materials well known in the art. Such materials should be non-toxic and should not interfere with the efficacy of the active ingredient. The carrier can take a wide variety of forms depending on the form of preparation desired for administration, e.g., intravenous, oral, intramuscular, subcutaneous, intrathecal, epineural or parenteral.

When the vectors of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation In another aspect of the invention, the vectors of the invention can be suitably formulated and introduced into the environment of the cell by any means that allows for a sufficient portion of the sample to enter the cell to induce gene silencing, if it is to occur. Many formulations for vectors are known in the art and can be used so long as the vectors gain entry to the target cells so that it can act.

For example, the vectors can be formulated in buffer solutions such as phosphate buffered saline solutions comprising liposomes, micellar structures, and capsids. The pharmaceutical formulations of the vectors of the invention can also take the form of an aqueous or anhydrous solution or dispersion, or alternatively the form of an emulsion or suspension. The pharmaceutical formulations of the vectors of the present invention may include, as optional ingredients, solubilizing or emulsifying agents, and salts of the type that are well-known in the art. Specific non-limiting examples of the carriers and/or diluents that are useful in the pharmaceutical formulations of the present invention include water and physiologically acceptable saline solutions. Other pharmaceutically acceptable carriers for preparing a composition for administration to an individual include, for example, solvents or vehicles such as glycols, glycerol, or injectable organic esters. A pharmaceutically acceptable carrier can contain physiologically acceptable compounds that act, for example, to stabilize or to increase the absorption of the shRNA encoding vector. Other physiologically acceptable carriers include, for example, carbohydrates, such as glucose, sucrose or dextrans, antioxidants, such as ascorbic acid or glutathione, chelating agents, low molecular weight proteins or other stabilizers or excipients, saline, dextrose solutions, fructose solutions, ethanol, or oils of animal, vegetative or synthetic origin. The carrier can also contain other ingredients, for example, preservatives.

It will be recognized that the choice of a pharmaceutically acceptable carrier, including a physiologically acceptable compound, depends, for example, on the route of administration of the composition. The composition containing the vectors can also contain a second reagent such as a diagnostic reagent, nutritional substance, toxin, or additional therapeutic agent. Many agents useful in the treatment of cardiac disease are known in the art and are envisioned for use in conjunction with the vectors of this invention.

Formulations of vectors with cationic lipids can be used to facilitate transfection of the vectors into cells. For example, cationic lipids, such as lipofectin, cationic glycerol derivatives, and polycationic molecules, such as polylysine, can be used. Suitable lipids include, for example, Oligofectamine and Lipofectamine (Life Technologies) which can be used according to the manufacturer's instructions.

Suitable amounts of vector must be introduced and these amounts can be empirically determined using standard methods. Typically, effective concentrations of individual vector species in the environment of a cell will be about 50 nanomolar or less 10 nanomolar or less, or compositions in which concentrations of about 1 nanomolar or less can be used. In other aspects, the methods utilize a concentration of about 200 picomolar or less and even a concentration of about 50 picomolar or less can be used in many circumstances. One of skill in the art can determine the effective concentration for any particular mammalian subject using standard methods.

The shRNA is preferably administered in a therapeutically effective amount. The actual amount administered, and the rate and time-course of administration, will depend on the nature and severity of the condition, disease or disorder being treated. Prescription of treatment, for example, decisions on dosage, timing, etc., is within the responsibility of general practitioners or specialists, and typically takes account of the disorder, condition or disease to be treated, the condition of the individual mammalian subject, the site of delivery, the method of administration and other factors known to practitioners. Examples of techniques and protocols can be found in Remington's Pharmaceutical Sciences 18th Ed. (1990, Mack Publishing Co., Easton, Pa.).

Alternatively, targeting therapies can be used to deliver the shRNA encoding vectors more specifically to certain types of cell, by the use of targeting systems such as antibodies or cell specific ligands. Targeting can be desirable for a variety of reasons, e.g., if the agent is unacceptably toxic, or if it would otherwise require too high a dosage, or if it would not otherwise be able to enter the target cells.

shRNA: Gene Therapy siRNA can also be delivered into mammalian cells, particularly human cells, by a gene therapy approach, using a DNA vector from which siRNA compounds in, e.g., small hairpin form (shRNA), can be transcribed directly. Recent studies have demonstrated that while double-stranded siRNAs are very effective at mediating RNAi, short, single-stranded, hairpin-shaped RNAs can also mediate RNAi, presumably because they fold into intramolecular duplexes that are processed into double-stranded siRNAs by cellular enzymes. This discovery has significant and far-reaching implications, since the production of such shRNAs can be readily achieved in vivo by transfecting cells or tissues with DNA vectors bearing short inverted repeats separated by a small number of (e.g., 3, 4, 5, 6, 7, 8, 9) nucleotides that direct the transcription of such small hairpin RNAs. Additionally, if mechanisms are included to direct the integration of the vector or a vector segment into the host-cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice.

Gene therapy is carried out according to generally accepted methods as are known in the art. See, for example, U.S. Pat. Nos. 5,837,492 and 5,800,998 and references cited therein. Vectors in the context of gene therapy are meant to include those polynucleotide sequences containing sequences sufficient to express a polynucleotide encoded therein. If the polynucleotide encodes an shRNA, expression will produce the antisense polynucleotide sequence. Thus, in this context, expression does not require that a protein product be synthesized. In addition to the shRNA encoded in the vector, the vector also contains a promoter functional in eukaryotic cells. The shRNA sequence is under control of this promoter. Suitable eukaryotic promoters include those described elsewhere herein and as are known in the art. The expression vector may also include sequences, such as selectable markers, reporter genes and other regulatory sequences conventionally used.

Accordingly, the amount of shRNA generated in situ is regulated by controlling such factors as the nature of the promoter used to direct transcription of the nucleic acid sequence, (i.e., whether the promoter is constitutive or regulatable, strong or weak) and the number of copies of the nucleic acid sequence encoding a shRNA sequence that are in the cell.

For expression of Sav1 shRNA, a promoter is operatively linked to a shRNA sequence. As used herein, the term "promoter" refers to a DNA sequence that regulates expression of the target gene sequence being operatively linked to the promoter sequence in a certain host cell. The term "operatively linked" means that one nucleic acid fragment is linked to another nucleic acid fragment so that the function or expression thereof is affected by the other nucleic acid fragment. The expression cassette of the present invention may further comprise various expression regulatory sequences such as an optional operator sequence for controlling transcription, a sequence encoding a suitable mRNA ribosome-binding site, and sequences controlling the termination of transcription and translation. The promoter used in the present invention may be a constitutive promoter that constitutively induces the expression of a target gene, or an inducible promoter that induces the expression of a target gene at a given position and time point. Specific examples of the promoter may include U6 promoter, CMV (cytomegalovirus) promoter, SV40 promoter, CAG promoter (Hitoshi Niwa et al., Gene, 108:193-199, 1991; and Monahan et al., Gene Therapy, 7:24-30, 2000), CaMV 35S promoter (Odell et al., Nature 313:810-812, 1985), Rsyn7 promoter (U.S. patent application Ser. No. 08/991,601), ubiquitin promoter (Christensen et al., Plant Mol. Biol. 12:619-632, 1989), ALS promoter (U.S. patent application Ser. No. 08/409,297) and the like. Also usable promoters are disclosed in U.S. Pat. Nos. 5,608,149, 5,608,144, 5,604,121, 5,569,597, 5,466,785, 5,399,680, 5,268,463, 5,608,142, etc.

The recombinant vector of the present disclosure may be introduced into a host cell, using a conventional method known in the art. The host cell may be employed for manipulation of the vector or as a means to transfer the vector to an individual. Preferably, intracellular incorporation of the vector into the host cell may be carried out by a conventional method known in the art, such as calcium chloride, microprojectile bombardment, electroporation, PEG-mediated fusion, microinjection, liposome-mediated method, and the like.

Examples of the host cell that can be utilized in the present invention may include, but are not limited to, prokaryotic cells such as *Escherichia coli, Bacillus subtilis, Streptomyces, Pseudomonas, Proteus mirabilis*, and *Staphylococcus*, lower eukaryotic cells such as fungi (e.g. *Aspergillus*), yeast (e.g. *Pichia pastoris*), *Saccharomyces cerevi-*

*siae, Schizosaccharomyces*, and *Neurospora crassa*, and higher eukaryotic cells such as insect cells, plant cells, mammalian cells. Preferably, the host cell may be human cells.

Meanwhile, standard recombinant DNA and molecular cloning techniques used in the present disclosure are well known in the art and can be found in the following literature: Sambrook, J., Fritsch, E. F. and Maniatis, T., Molecular Cloning: A Laboratory Manual, 2nd ed., Cold Spring Harbor Laboratory: Cold Spring Harbor, N.Y. (1989); Silhavy, T. J., Bennan, M. L. and Enquist, L. W., Experiments with Gene Fusions, Cold Spring Harbor Laboratory: Cold Spring Harbor, N.Y. (1984); and Ausubel, F. M. et al., Current Protocols in Molecular Biology, published by Greene Publishing Assoc. and Wiley-Interscience (1987).

The pharmaceutical composition according to the present invention may comprise a therapeutically effective amount of the recombinant vector of the present invention and a cardiac drug alone or in combination with one or more pharmaceutically acceptable carriers. As used herein, the term "therapeutically effective amount" refers to an amount which is capable of producing the desired therapeutic response greater than that exhibited by a negative control. Preferably, the therapeutically effective amount is a dose sufficient to prevent or treat the cardiovascular disease.

A therapeutically effective amount of the recombinant vector in the present disclosure may be in a range of 0.0001 to 100 mg/day/kg (BW), preferably 0.005-0.05 mg/day/kg. However, an effective dose of the drug may vary depending upon various factors such as kinds and severity of disease, age, weight, health and sex of patients, administration routes and treatment duration.

As used herein, the term "pharmaceutically acceptable" means that the compound is physiologically acceptable, and does not cause allergic reactions (such as gastrointestinal disorders, and vertigo) or similar reactions with no inhibitory effects on the action of an active ingredient, when it is administered to humans or animals. Examples of the pharmaceutically acceptable carrier may include all kinds of solvents, dispersion media, oil-in-water or water-in-oil emulsions, aqueous compositions, liposomes, microbeads and microsomes.

Meanwhile, the pharmaceutical composition of the present invention may be appropriately formulated in conjunction with any suitable carrier by a conventional method known in the art, depending upon administration routes of the drug. There is no particular limit to the administration route of the pharmaceutical composition. Therefore, the drug composition in accordance with the present invention may be administered via oral or parenteral routes. Examples of the parenteral administration route may include transdermal, intranasal, intraperitoneal, intramuscular, subcutaneous and intravenous routes.

When the pharmaceutical composition of the present invention is administered via an oral route, the pharmaceutical composition in conjunction with any orally acceptable vehicle may be formulated into various dosage forms such as powders, granules, tablets, pills, dragees, capsules, solutions, gels, syrups, suspensions, and wafers, according to a conventional method known in the art. Examples of suitable vehicles may include various kinds of fillers, for example sugars such as lactose, dextrose, sucrose, sorbitol, mannitol, xylitol, erythritol and maltitol; starches such as corn starch, wheat starch, rice starch and potato starch; cellulose substances such as cellulose, methyl cellulose, sodium carboxymethyl cellulose and hydroxypropyl methyl cellulose; gelatin, polyvinylpyrrolidone (PVP) and the like. If desired, there may be added disintegrating agents such as cross-linked polyvinylpyrrolidone, agar, and alginic acid or sodium alginate. Further, the pharmaceutical composition may further comprise anticoagulants, lubricants, wetting agents, fragrances, emulsifiers and preservatives.

When the pharmaceutical composition of the present invention is administered via a parenteral route, the pharmaceutical composition in conjunction with any parenterally acceptable vehicle may be formulated into, for example, an injectable preparation, a transdermal preparation or a nasal inhalant, according to a conventional method known in the art. Upon formulation of the injectable preparation, sterilization must be performed in conjunction with protection of the pharmaceutical preparation from microbial contamination including pathogenic bacteria and fungi. Examples of the vehicle suitable for the injectable preparation may include, but are not limited to, solvents or dispersion media including water, ethanol, polyols (such as glycerol, propylene glycol, and liquid polyethylene glycol), mixtures thereof and/or vegetable oil. More preferably, examples of the suitable vehicle may include isotonic solutions such as Hank's solution, Ringer's solution, PBS (phosphate buffered saline) containing triethanolamine, sterile water for injection, 10% ethanol, 40% propylene glycol and 5% dextrose. In order to protect the injectable preparation against microbial contamination, the preparation may further comprise various antibacterial and antifungal agents, for example, parabens, chlorobutanol, phenol, sorbic acid, thimerosal, and the like. In many cases, it will be preferable to include isotonic agents, for example, sugar or sodium chloride.

In the case of the transdermal formulation, the inventive pharmaceutical composition may be formulated in the form of ointments, creams, lotions, gels, external solutions, pastes, liniments, or aerosols. The term "transdermal administration" means that a therapeutically effective amount of an active ingredient contained in a pharmaceutical composition transmits into the skin when the pharmaceutical composition is topically applied to the skin. These formulations are described in the literature that is a guidebook generally known in all pharmaceutical chemistry fields (Remington's Pharmaceutical Sciences, 15.sup.th Edition, 1975, Mack Publishing Company, Easton, Pa.).

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gases. In the case of a pressurized aerosol, the dosage unit may be determined by providing a valve to deliver a metered amount. Capsules and cartridges of, e.g., gelatin for use in an inhaler or insufflator may be formulated containing a powdered mixture of the compound and a suitable powder base such as lactose or starch.

Other pharmaceutically acceptable vehicles can be found in the literature (Remington's Pharmaceutical Sciences, 19.sup.th ed., Mack Publishing Company, Easton, Pa., 1995).

The pharmaceutical composition of the present invention may further comprise one or more buffers (e.g. saline or PBS), carbohydrates (e.g. glucose, mannose, sucrose or dextran), antioxidants, bacteriostatic agents, chelating agents (e.g. EDTA or glutathione), adjuvants (e.g. aluminum hydroxide), suspending agents, thickening agents, and/or preservatives.

Additionally, the pharmaceutical composition of the present invention may be appropriately formulated by a conventional method known in the art, such that it is possible to achieve fast, sustained or delayed release of active ingredients after administration of the composition to a mammal.

Further, the pharmaceutical composition of the present invention may be administered in combination with a known drug having therapeutic effects for treating a cardiac condition.

EXAMPLES

The following examples are included to demonstrate certain non-limiting aspects of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention

Example 1

Hippo Signaling Promotes Adult Cardiomyocyte Renewal

While other organs have regenerative capacity, cardiomyocytes fail to renew or to regenerate sufficiently to repair the damaged heart (Kikuchi and Poss, 2012). To investigate the hypothesis that Hippo-signaling is a negative regulator of postnatal cardiomyocyte renewal, we inactivated Salv and both Lats genes in adult cardiomyocytes.

To test the role of Salv, Lats1, and Lats2 in adult cardiomyocytes, conditional null alleles were used for Hippo genes and the Myh6$^{creERT2}$ transgene that directs tamoxifen-regulated cardiomyocyte cre activity (Sohal et al., 2001). Because the heart contains multiple cell types, cardiomyocytes were visualized using the R26$^{mTmG}$ (mTmG) allele, which expresses eGFP upon cre activation, to trace the cardiomyocyte lineage (Muzumdar et al., 2007). Adult cardiomyocytes were generated that were mutant for Salv and Lats1/2 by injecting three month-old mice with tamoxifen (Heallen et al., 2013). To determine if Hippo deficiency results in cell cycle reentry, mice were injected with 5-ethynyl-2'-deoxyuridine (EdU). Nuclear EdU incorporation, indicating de novo DNA synthesis, was detected in both Salv conditional knock out (CKO) and Lats1/2 CKO mutant cardiomyocytes revealing an endogenous cardiomyocyte renewal capacity when Hippo-signaling is deleted. Quantification of EdU positive cells showed significant induction of DNA synthesis in Hippo-deficient hearts with a greater increase in Lats1/2 mutants compared to Salv CKO cardiomyocytes (Heallen et al., 2013). Cell cycle reentry was also quantified in isolated cardiomyocyte nuclei using FACS analysis (Bergmann et al., 2009; Heallen et al., 2013). Both Lats1/2 CKO and Salv CKO cardiomyocyte nuclei had increased numbers of Ki-67 expressing cardiomyocytes compared to controls (Heallen et al., 2013). These results show that cardiomyocytes re-enter the cell cycle upon Hippo pathway disruption, supporting the hypothesis that Hippo-signaling is a negative regulator of adult cardiomyocyte renewal.

It was evaluated whether Salv CKO and Lats1/2 CKO cardiomyocytes progress through mitosis and cytokinesis Immunohistochemistry was performed with the M-phase marker Aurora B kinase (Aurkb) to determine if cytokinesis occurred in Hippo-deficient cardiomyocytes. Aurkb expression in Lats1/2 and Salv CKO cardiomyocytes was clearly detectable at the cleavage furrow providing direct evidence for cytokinesis (Heallen et al., 2013). In contrast to Hippo-deficient hearts, Aurkb expression was not detected in control hearts.

In summary, Hippo pathway inactivation in the unstressed adult mouse heart results in enhanced cardiomyocyte renewal with increased myocardial S-phase entry and progression through mitosis (Heallen et al., 2013). These findings uncover an inhibitory role for Hippo-signaling in adult cardiomyocyte renewal.

Example 2

Hippo Signaling Promotes Adult Heart Regeneration in an Acute Injury Model

Cardiac apex resection in the first six days of life results in cardiac regeneration while resections performed at postnatal day (P) 7 and later results in fibrosis and scarring (Porrello et al., 2011).

To test regenerative capability, apex resection was performed of uniform size at the normally non-regenerative P8 stage in control and Hippo-deficient hearts. To inactivate Salv, mice were injected with four tamoxifen doses prior to and after the resection. Both GFP fluorescence, detecting recombination in the mTmG reporter, and immunofluorescence with an anti-Salv antibody indicated efficient deletion of Salv in mutant myocardium at four days post resection (4 dpr). Evaluation of 21 dpr hearts by serial sectioning revealed severe scarring of control hearts in all but a few cases. In contrast, resected Hippo-deficient hearts efficiently regenerated the myocardium with reduced scar size (Heallen et al., 2013). The regenerated cardiac apex was derived primarily from pre-existing cardiomyocytes.

Left anterior descending (LAD) coronary artery occlusion was performed at both P8 and two months of age. In P8 hearts, following LAD occlusion (LADO) there was functional recovery and reduced scar size when analyzed at twenty one days after occlusion. Histology also confirmed the recovery of myocardium with less scar tissue after LADO (Heallen et al., 2013). In adult hearts, there was similarly strong histologic and functional evidence for cardiomyocyte regeneration after LADO. Fractional Shortening and Ejection Fraction evaluated by echocardiography indicated that by three weeks post LADO, adult Hippo-deficient hearts had recovered function comparable to that of sham operated animals suggesting that Hippo-deficient cardiomyocytes have increased survival and/or proliferation after ischemic damage (Heallen et al., 2013).

Example 3

Hippo-Deficient Cardiomyocytes Extensively Proliferate and Acquire Migratory Properties During Regeneration Four dpr (P12) Hippo-deficient hearts were evaluated in more depth. Four hours prior to harvest, hearts were pulsed with EdU to visualize cells that had entered the cell cycle. In control hearts, EdU-positive cells were primarily found in the GFP negative, non-cardiomyocyte lineage near the resected zone and most likely are infiltrating inflammatory cells and proliferating cardiac fibroblasts. Similar proliferating GFP-negative cells were also observed in Salv CKO hearts. In contrast to controls, Salv CKO resected hearts had EdU/GFP double positive cardiomyocytes within both the border zone and distal heart regions (Heallen et al., 2013; Morikawa et al., 2014).

Hippo-deficiency enhances the ability of cardiomyocytes to re-enter the cell cycle throughout the whole heart. In Salv CKO mutant hearts, cells derived from the cardiomyocyte lineage detached from surrounding border zone cardiomyocytes and entered the resected zone that contained a large number of non-cardiomyocyte cells. Moreover, Hippo-deficient GFP-positive myocardial derived cells extended lamellipodia-like protrusions. In control hearts, GFP positive cells grouped together within the border zone and did not infiltrate the resected region of the heart (Morikawa et al., 2014).

Example 4

Figure 2B:
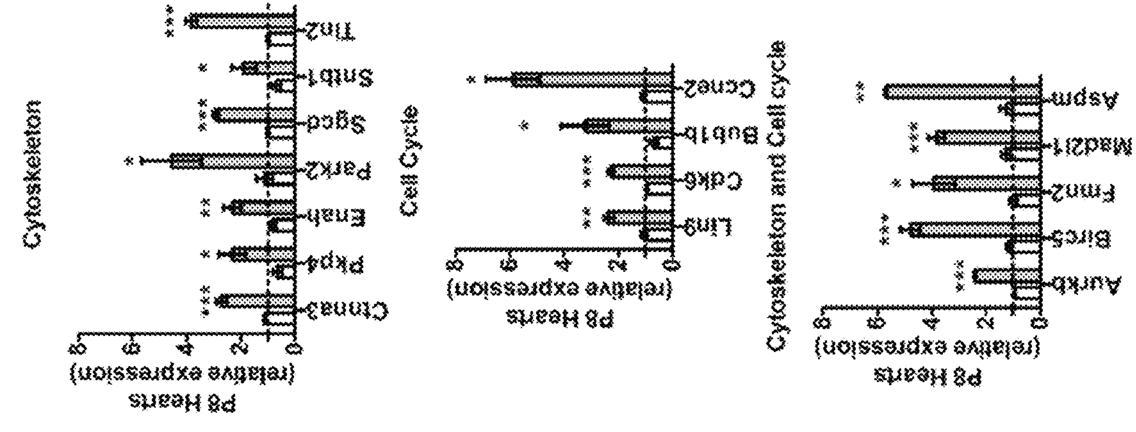
FIGS. 2A and 2B shows that Yap regulates cell division and motility genes in cardiac regeneration. Heat maps (FIG. 2A) and qRT-PCR validation (FIG. 2B) showing relative transcript levels for a subset of Yap targets. *$p<0.05$, $p<0.001$, *$p<0.0001$. Adapted from (Morikawa et al., 2014)
Figure 2A:
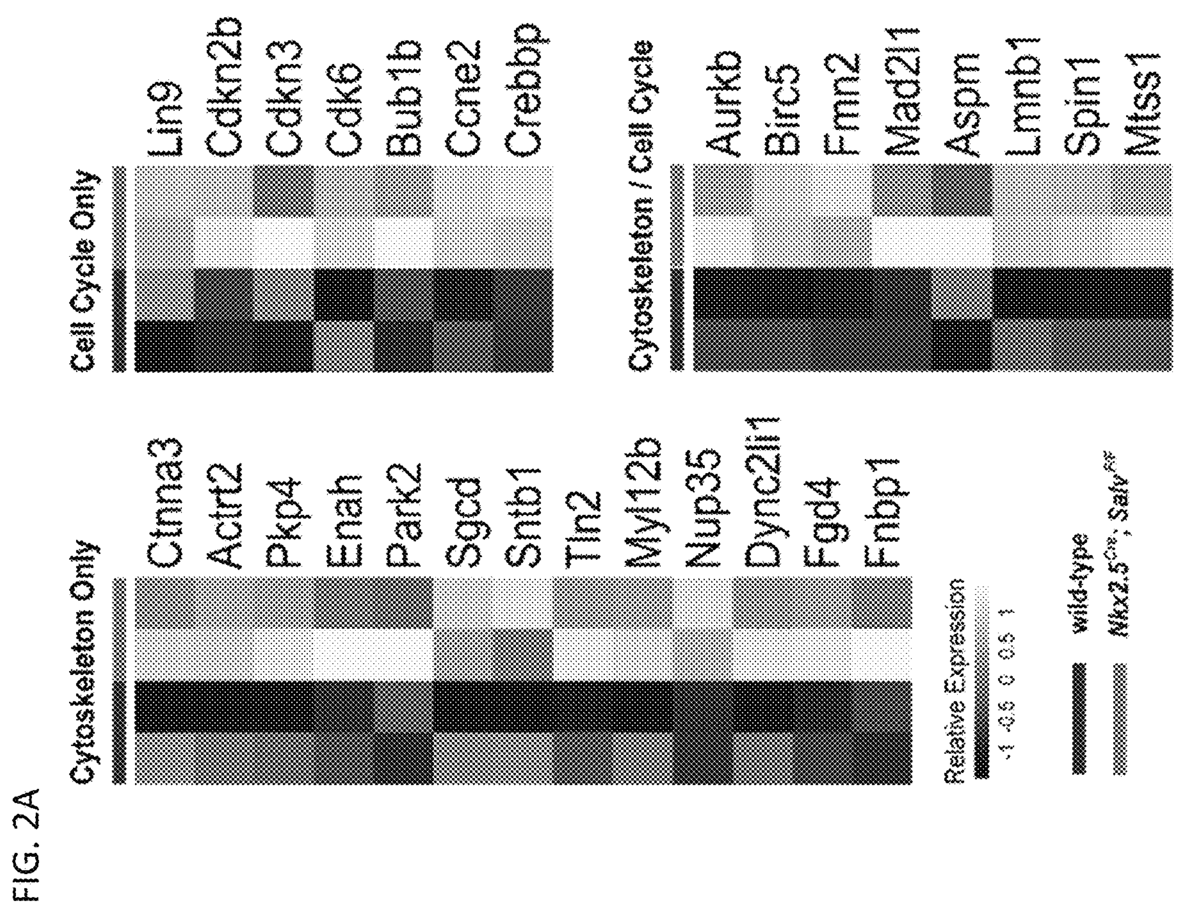

Yap Directly Regulates Genes that Promote Cell Cycle Progression and Cytoskeletal Remodeling To gain further insight into the direct targets of Hippo-signaling in cardiac regeneration, chromatin immunoprecipitation sequencing (ChIP-seq) experiments were performed using an antibody against the Hippo effector Yap. We used mRNA expression data from microarray experiments to overlay the ChIP-seq dataset with upregulated genes in Nkx2.5$^{cre}$ Salv mutant hearts (FIGS. 2A-2B). Gene expression changes were validated by qRT-PCR experiments (FIG. 2B). Gene Ontology analysis indicated that Yap directly regulates genes involved in cell cycle progression and cytoskeletal dynamics (FIG. 2A and (Morikawa et al., 2014)). Also included among Yap regulated cell cycle genes are cyclin dependent kinases, such as Cdk6, and the previously validated Yap target, CyclinE2. Another Yap target, the cell cycle gene Lin9, is a member of the MuvB complex, which enhances the G2/M transition (Kleinschmidt et al., 2009; Sadasivam et al., 2012) (FIGS. 2A-2B).

Yap target genes regulating both cytoskeletal and cell cycle progression include Aurkb and Birc5 (survivin) (FIGS. 2A-2B). Both Aurkb and Birc5 are chromosome passenger complex components and are important for chromosome condensation and segregation during mitosis, as well as for cytokinesis. Importantly, Birc5 was shown previously to be regulated by Hippo-signaling in the developing heart (Heallen et al., 2011). Genes expressed in the cytokinetic furrow and spindle midzone that regulate cytokinesis, such as Anillin, Pkp4, and Ect2 are direct Yap target genes, indicating that Yap promotes cytokinesis in regenerating cardiomyocytes (Hesse et al., 2012; Matthews et al., 2012; Wolf et al., 2006).

Example 5

Yap Directly Regulates Genes that Promote Cytoskeletal Remodeling and Cell Motility During Cardiac Regeneration Consistent with the dramatic changes in cell morphology, we found that Yap also directly binds genes that regulate the actin cytoskeleton (FIGS. 2A-2B). A number of Yap regulated targets are known to localize to lamellipodia and filopodia such as Enah, an Ena/VASP actin regulator that causes cardiac dysfunction when disrupted in mice (Mejillano et al., 2004; Morikawa et al., 2014).

Yap also binds genes involved in force transmission between cardiomyocytes and the extracellular matrix (ECM). These include genes that are implicated in connecting actin cytoskeleton to the cytoplasmic membrane. Sarcoglycan delta (Sgcd) and Syntrophin B1 (Sntb1) are both components of the dystrophin glycoprotein complex (DGC), which is important for connecting the actin cytoskeleton to the ECM and may transmit force between muscle cells (Barton, 2006; Goyenvalle et al., 2011). Both genes are mutated in human patients with muscular dystrophy and stabilize the plasma membrane in response to mechanical stress. The actin binding protein, Talin2, connects the actin cytoskeleton to integrins and the ECM. Lastly, Ctnna3, a cadherin-associated gene expressed in the intercalated disc (ICD), connects the actin cytoskeleton to both the ICD and the ECM and likely senses tension between cardiomyocytes (Li et al., 2012).

Example 6

Figure 3:
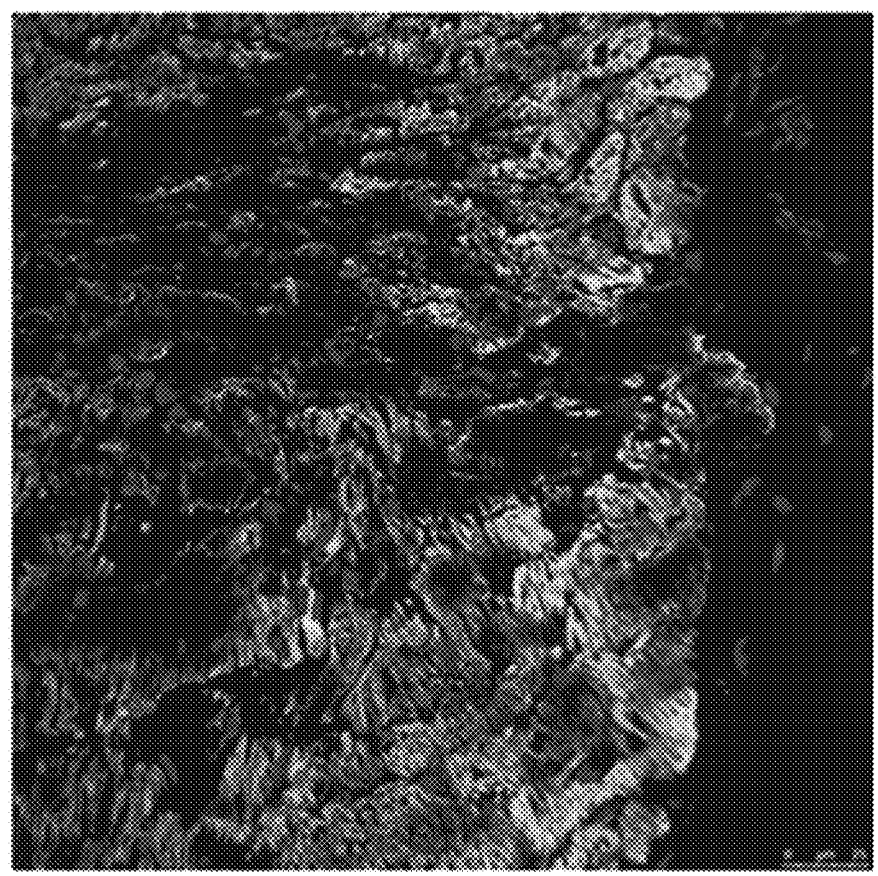
FIG. 3 shows Salv CKO and Salv CKO; mdx; utrn hearts after apex resection. Hearts were resected at postnatal day 8, a non-regenerative stage, and evaluated by immunohistochemistry at three weeks after resection. The Salv CKO mutant hearts can regenerate as reported (left hand panel and (Heallen et al., 2013). In addition, the compound mutant SalvCKO; mdx−; utrn+/−hearts can also regenerate as shown in the panel on the right. Notably, mdx mutant hearts fail to regenerate after cardiomyocyte resection.
Figure 3:
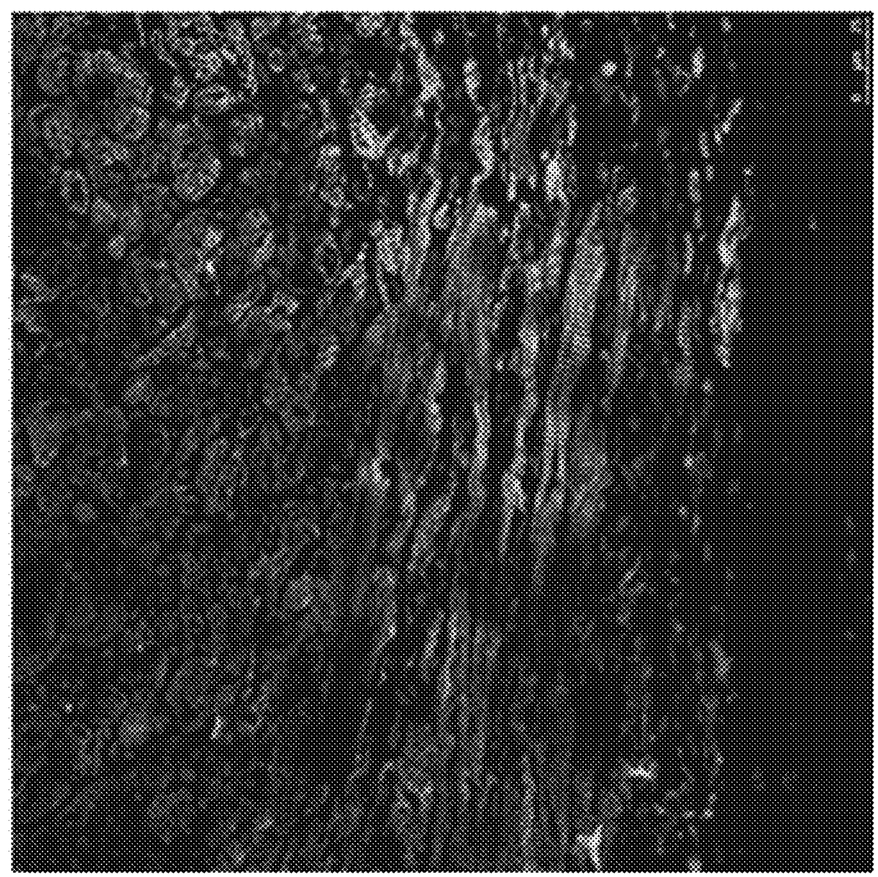

Hippo Depletion Rescues the Cardiac Regeneration Defect in MDX Mutant Hearts To determine whether Hippo pathway loss of function could suppress the mdx failed regeneration phenotype, we generated Salv; mdx double mutant hearts and performed apex resection at postnatal day 8 on double mutants and control samples. As shown in FIG. 3, the Salv CKO and Salv; mdx double mutants regenerated the myocardium in contrast to the mdx mutants that cannot regenerate myocardium (Morikawa et al., 2014). This indicates that Hippo depletion, with resultant Yap upregulation and Yap target gene upregulation, can suppress the mdx heart phenotype. Our findings indicate that Hippo depletion in myocardium is a promising approach to treat DMD cardiomyopathy.

Example 7

Figure 4:
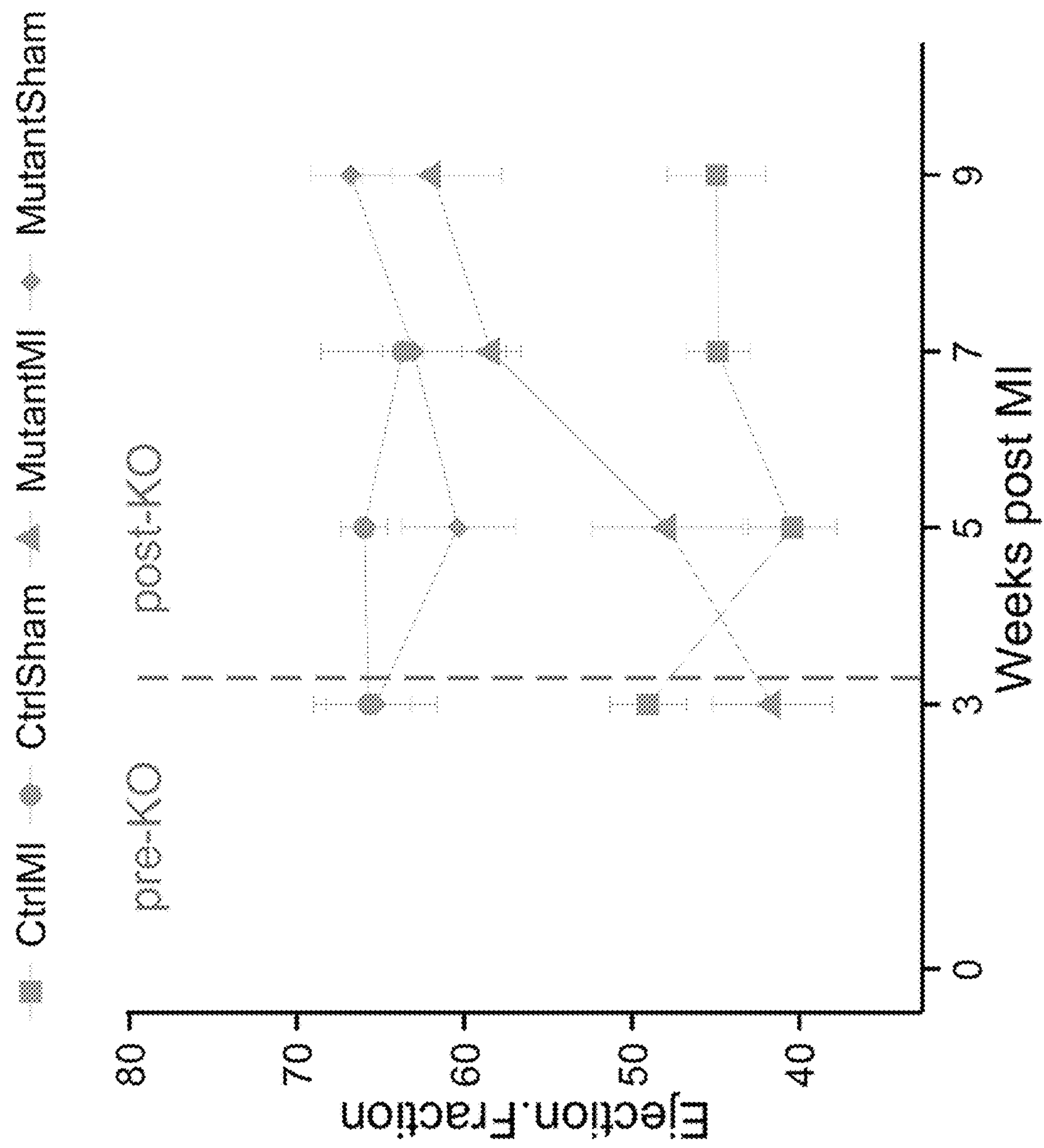
FIG. 4 demonstrates that Hippo depletion promotes cardiac functional recovery after chronic ischemia and established heart failure. Adult hearts were subjected to LAD-O (t=0) and studied by echocardiography three weeks later. Hearts that were in failure were entered into the study and tamoxifen was injected to inactivate Salv. Mice were studied by echocardiography at two-week intervals as shown. Hippo deficient hearts showed recovery of function at two-weeks post tamoxifen injection and by six weeks functional recovery was complete.

Hippo Deletion Promotes Cardiomyocyte Regeneration in the Context of Established Heart Failure It was determined whether Hippo pathway inactivation three weeks after myocardial infarct still promotes cardiomyocyte regeneration with improved cardiac function. This is a clinically important question since many patients suffer from chronic infarcts that lead to pathologic cardiac remodeling with heart failure and death. Previous to this it was unknown whether Hippo deletion could effectively promote heart regeneration in the context of an established mature scar. A myocardial infarct was introduced into the hearts of control and uninjected Salv CKO hearts at time point zero (FIG. 4). The uninjected Salv CKO mice still express control levels of Salv. Sham controls were also established at time zero. Three weeks after infarction all mice were carefully studied by echocardiography and operated mice that were in heart failure with reduced EF were included in the study and received a tamoxifen injection to inactivate the Hippo pathway.

Cardiac function parameters were evaluated in all hearts at two-week intervals after tamoxifen injection (FIG. 4). The Salv CKO mutants had functional recovery starting at the two-week timepoint (5 weeks post MI) and function continued to improve until it reached the level of un-operated controls (9 weeks post MI). Hippo pathway inactivation after established heart failure results in cardiac repair with return of cardiac function.

Example 8

Figure 5:
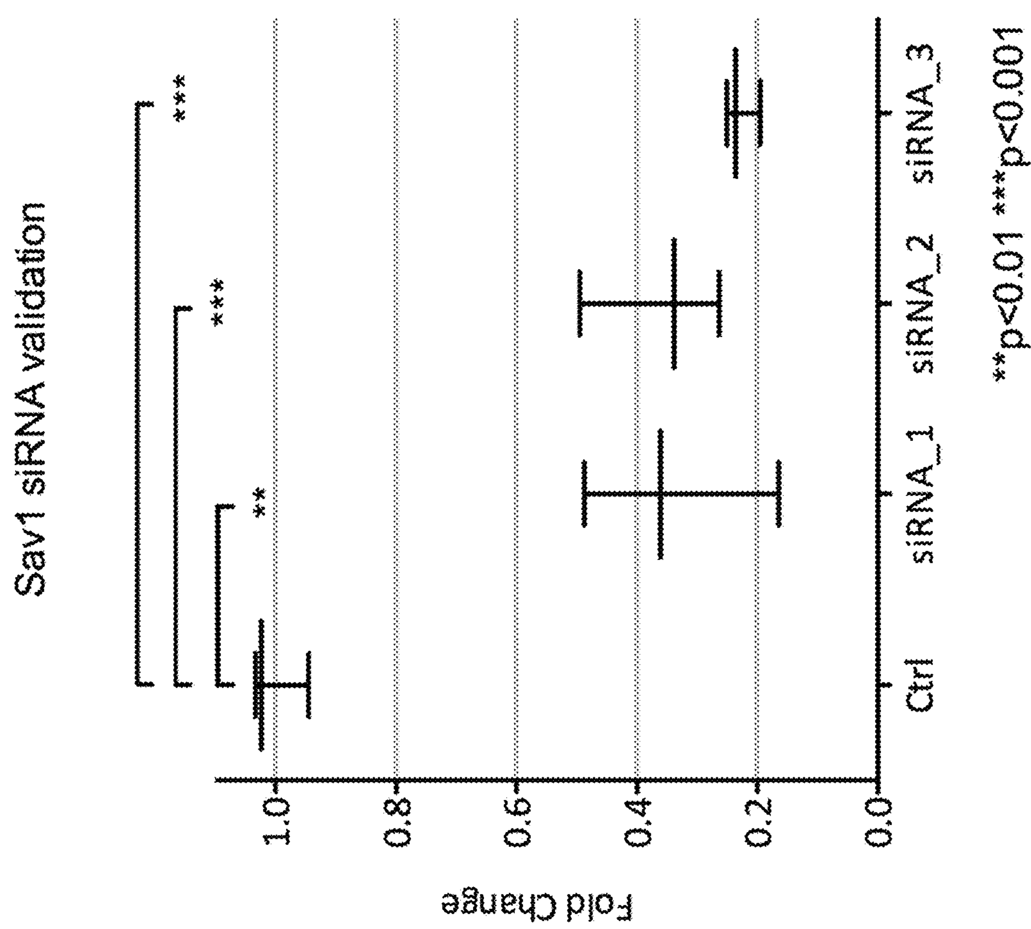
FIG. 5 shows that Salv siRNA effective reduces Salv mRNA expression. siRNAs were transfected into neonatal cardiomyocytes and Salv mRNA levels were studied by quantitative RT PCR. All three siRNAs effectively reduced Salv mRNA levels.

Design of Small Hairpin RNAs (shRNA) to Inactivate the Hippo Pathway in the Adult Heart Three examples of shRNAs against Salv in regions of the molecule that are conserved between mouse, human, and swine so that they can be interchangeably used between these three species using standard methods ((Tafer, 2014); FIGS. 6, 7, and 8). The functional efficiency of each shRNA was validated, using siRNA knockdown experiments, to suppress endogenous Salv expression in neonatal cardiomyocytes (FIG. 5). All three shRNAs effectively knocked down Salv expression approximately 70% with shRNA #3 providing the greatest knockdown efficiency.

REFERENCES

Barton, E. R. (2006). Impact or sarcoglycan complex on mechanical signal transduction in murine skeletal muscle. American journal of physiology Cell physiology 290, C411-419.

Bergmann, O., Bhardwaj, R. D., Bernard, S., Zdunek S., Barnabe-Heider, F., Walsh, S., Zupicich, J., Alkass, K., Buchholz, B. A., Druid, et al. (2009). Evidence for cardiomyocyte renewal in humans. Science 324, 98-102.

Bulfield, G., Siller, W. G., Wight, P. A., and Moore, K. J. (1984). X chromosome-linked muscular dystrophy (mdx) in the mouse Proc Natl Acad Sci USA 81, 1189-1192.

Emery, A. E. (2002). The muscular dystrophies. Lancet 359, 657-695.

Goyenvalle, A., Seto, J. T., Davies, K. E., and Chamberlain, J. (2011). Therapeutic approaches to muscular dystrophy. Hum Mol Genet 20, R69-78.

Halder, G., and Johnson, R. L. (2011). Hippo signaling: growth control and beyond. Development 138, 9-22.

Heallen, T., Morikawa, Y., Leach, J., Tao, G., Willerson, J. T., Johnson, R. L., and Martin, J. F. (2013). Hippo signaling impedes adult heart regeneration. Development 140, 4683-4690.

Heallen, T., Zhang, M., Wang, J., Bonilla-Claudio, M., Klysik, E., Johnson, R. L., and Martin, J. F. (2011). Hippo pathway inhibits Wnt signaling to restrain cardiomyocyte proliferation and heart size. Science 332, 458-461.

Hesse, M., RaulF, A., Pilz, G. A., Haberlandt, C., Klein, A. M., Jabs, R., Zaehres, H., Fugemann, C. J., Zimmermann, K., Trebicka, J., et al. (2012). Direct visualization of cell division using high-resolution imaging of M-phase of the cell cycle. Nature communications 3, 1076.

Hoffman, E. P., Brown, R. H., Jr., and Kunkel, L. M. (1987). Dystrophin: the protein product of the Duchenne muscular dystrophy locus. Cell 51, 919-928.

Hoffman, E. P., Hudecki, M. S., Rosenberg, P. A., Pollina, C. M., and Kunkel, L. M. (1988). Cell and fiber-type distribution of dystrophin. Neuron 1, 411-420.

Kikuchi, K., and Poss, K. D. (2012). Cardiac regenerative capacity and mechanisms. Annual review of cell and developmental biology 28, 719-741.

Kleinschmidt, M. A., Wagner, T. U., Liedtke, D., Spahr, S., Samans, B., and Gaubatz, S. (2009). lin9 is required for mitosis and cell survival during early zebrafish development. The Journal of biological chemistry 284, 13119-13127.

Li, J., Goossens, S., van Hengel, J., Gao, E., Cheng, L., Tyberghein, K., Shang, X., De Rycke, R., van Roy, F., and Radice, G. L. (2012). Loss of alphaT-catenin alters the hybrid adhering junctions in the heart and leads to dilated cardiomyopathy and ventricular arrhythmia Following acute ischemia. Journal of cell science 125, 1058-1067.

Matthews, H. K., Delabre, U., Rohn, J. L., Guck, J., Kunda, P., and Baum, B. (2012). Changes in Ect2 localization couple actomyosin-dependent cell shape changes to mitotic progression. Dev Cell 23, 371-383.

Mejillano, M. R., Kojima, S., Applewhite, D. A., Gertler, F. B., Svitkina, T. M., and Borisy, G. G. (2004). Lamellipodial versus filopodial mode of the actin nanomachinery: pivotal role of the filament barbed end. Cell 118, 363-373.

Morikawa, Y., Zhang, M., Heallen, T., Leach, J., Tao, G., Xiao, Y., Bai, Y., Willerson, J. T., and Martin, J. F. (2014). Actin cytoskeletal remodeling with protrusion formation is essential for heart regeneration in Hippo deficient mice. submitted.

Muzumdar, M. D., Tasic, B., Miyamichi, K., Li, L., and Luo, L. (2007). A global double-fluorescent Cre reporter mouse. Genesis 45, 593-605.

Ohlendieck, K., and Campbell, K. P. (1991). Dystrophin-associated proteins are greatly reduced in skeletal muscle from mdx mice. J Cell Biol 115, 1685-1694.

Ohlendieck, K., Matsumura, K., Ionasescu, V. V., Towbin, J. A., Bosch, E. P., Weinstein, S. L., Sernett, S. W., and Campbell, K. P. (1993). Duchenne muscular dystrophy: deficiency of dystrophin-associated proteins in the sarcolemma. Neurology 43, 795-800.

Piras, B A., O'Connor, D. M., French, B. A. (2013). Systemic Delivery of shRNA by AAV9 Provides Highly Efficient Knockdown of Ubiquitously Expressed GFP in ouse Heart, but Not Liver. PLOS One 8(9), 1-11.

Porrello, E. R., Mahmoud, A. I., Simpson, E., Hill, J. A., Richardson, J. A., Olson, E. N., and Sadek, H. A. (2011). Transient regenerative potential of the neonatal mouse heart. Science 331, 1078-1080.

Sadasivam, S., Duan, S., and DeCaprio, J. A. (2012). The MuvB complex sequentially recruits B-Myb and FoxM1 to promote mitotic gene expression. Genes Dev 26, 474-489.

Sohal, D. S., Nghiem, M., Crackower, M. A., Witt, S. A., Kimball, T. R., Tymitz, K. M., Penninger, J. M., and Molkentin, J. D. (2001). Temporally regulated and tissue-specific gene manipulations in the adult and embryonic heart using a tamoxifen-inducible Cre protein. Circ Res 89, 20-25.

Tarer, H. (2014). Bioinformatics of siRNA design. Methods in molecular biology (Clifton, N. J.) 1097, 477-490.

von Gise, A., Lin, Z., Schlegelmilch, K., Honor, L. B., Pan, G. M., Buck, J. N., Ma, Q., Ishiwata, T., Zhou, B., Camargo, F. D., et al. (2012). YAP1, the nuclear target of Hippo signaling, stimulates heart growth through cardiomyocyte proliferation but not hypertrophy. Proc Natl Acad Sci USA 109, 2394-2399.

Wolf, A., Keil, R., Gotzl, O., Mun, A., Schwarze, K., Lederer, M., Huttelmaier, S., and Hatzfeld, M. (2006). The armadillo protein p0071 regulates Rho signalling during cytokinesis. Nature cell biology 8, 1432-1440.

Xin, M., Kim, Y., Sutherland, L. B., Qi, X., McAnally, J., Schwartz, R. J., Richardson, J. A., Bassel-Duby, R., and Olson, E. N. (2011). Regulation of insulin-like growth factor signaling by Yap governs cardiomyocyte proliferation and embryonic heart size. Science signaling 4, ra70.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An isolated synthetic nucleic acid composition comprising:

(i) a sequence comprising SEQ ID NO: 10 or a derivative nucleic acid comprising at least 80% identity to SEQ ID NO: 10, and an antisense sequence thereof; and/or (ii) a sequence comprising SEQ ID NO: 11 or a derivative nucleic acid comprising at least 80% identity to SEQ ID NO: 11, and an antisense sequence thereof; and/or (iii) a sequence comprising SEQ ID NO: 12 or a derivative nucleic acid comprising at least 80% identity to SEQ ID NO: 12, and an antisense sequence thereof;

wherein when the sequence and the antisense sequence are hybridized together to form a duplex structure, the sequence and the antisense sequence are separated by a loop structure.

2. The composition of claim 1, wherein the derivative nucleic acid is at least 85%, 90%, 95%, 96%, 97%, 98%, or 99% identical to one of SEQ ID NO: 10, SEQ ID NO: 11, or SEQ ID NO: 12.

3. The composition of claim 1, wherein said nucleic acid is at least 43 nucleotides in length.

4. The composition of claim 1, wherein said nucleic acid is no more than 137 nucleotides in length.

5. The composition of claim 1, wherein the loop structure is between 5 and 19 nucleotides in length.

6. The composition of claim 1, wherein the derivative nucleic acid has 1, 2, 3, 4, or 5 mismatches compared to the respective SEQ ID NO: 10, SEQ ID NO: 11, or SEQ ID NO: 12.

7. The composition of claim 1, wherein the nucleic acid or derivative nucleic acid is comprised in a vector.

8. The composition of claim 7, wherein the vector is a viral vector.

9. The composition of claim 8, wherein the viral vector is an adeno-associated viral (AAV) vector.

10. The composition of claim 9, wherein the viral vector is an AAV9 vector.

11. The composition of claim 7, wherein the nucleic acid is operably linked to a tissue-specific or cell-specific promoter.

12. The composition of claim 11, wherein the promoter is a cardiomyocyte-specific promoter selected from the group consisting of: a rat ventricle-specific cardiac myosin light chain 2 (MLC-2v) promoter; a cardiac muscle-specific alpha myosin heavy chain (MHC) gene promoter; a cardiac cell-specific minimum promoter from −137 to +85 of NCX1 promoter; a chicken cardiac troponin T (cTNT); and a combination thereof.

13. The composition of claim 7, wherein two or more of nucleic acids comprising SEQ ID NO: 10, SEQ ID NO: 11, or SEQ ID NO: 12 are present on the same vector.

14. The composition of claim 13, wherein the two or more nucleic acids are regulated by the same regulatory sequence.

15. The composition of claim 14, wherein each of the two or more nucleic acids is regulated by a different regulatory sequence.

16. A method of promoting cardiomyocyte regeneration in an individual, the method comprising administering to the individual an effective amount of the composition of claim 1.

17. The method of claim 16, wherein the heart of the individual has cardiomyocyte apoptosis, necrosis, and/or autophagy.

18. The method of claim 17, wherein the individual has a cardiac condition selected from the group consisting of: cardiovascular disease, cardiomyopathy, heart failure, myocardial infarction, ischemia, necrosis, fibrosis, diabetic cardiomyopathy, and age-related cardiomyopathy.

19. The method of claim 17, wherein the composition is administered locally to the heart of the individual.

* * * * *

UNITED STATES PATENT AND TRADEMARK OFFICE

CERTIFICATE OF CORRECTION

PATENT NO. : 11,459,565 B2
APPLICATION NO. : 17/096260
DATED : October 4, 2022
INVENTOR(S) : James F. Martin et al.

It is certified that error appears in the above-identified patent and that said Letters Patent is hereby corrected as shown below:

On the Title Page

(73) Assignee should read: Baylor College of Medicine, Houston TX (US)
Texas Heart Institute, Houston, TX (US)

Signed and Sealed this
Twenty-eighth Day of November, 2023

Katherine Kelly Vidal

Katherine Kelly Vidal
*Director of the United States Patent and Trademark Office*